United States Patent
Sivaramakrishnan et al.

(10) Patent No.: US 12,098,184 B2
(45) Date of Patent: Sep. 24, 2024

(54) G PROTEIN-COUPLED RECEPTOR (GPCR) LIGAND ASSAY

(71) Applicant: REGENTS OF THE UNIVERSITY OF MINNESOTA, Minneapolis, MN (US)

(72) Inventors: Sivaraj Sivaramakrishnan, North Oaks, MN (US); Keehun Kim, Minneapolis, MN (US)

(73) Assignee: Regents of the University of Minnesota, Minneapolis, MN (US)

(*) Notice: Subject to any disclaimer, the term of this patent is extended or adjusted under 35 U.S.C. 154(b) by 870 days.

(21) Appl. No.: 16/769,852

(22) PCT Filed: Dec. 4, 2018

(86) PCT No.: PCT/US2018/063827
§ 371 (c)(1),
(2) Date: Jun. 4, 2020

(87) PCT Pub. No.: WO2019/113054
PCT Pub. Date: Jun. 13, 2019

(65) Prior Publication Data
US 2021/0179692 A1    Jun. 17, 2021

Related U.S. Application Data

(60) Provisional application No. 62/646,534, filed on Mar. 22, 2018, provisional application No. 62/594,356, filed on Dec. 4, 2017.

(51) Int. Cl.
| | | |
|---|---|---|
| *C07K 14/72* | (2006.01) | |
| *G01N 33/542* | (2006.01) | |
| *G01N 33/566* | (2006.01) | |
| *G01N 33/68* | (2006.01) | |

(52) U.S. Cl.
CPC ......... *C07K 14/723* (2013.01); *G01N 33/542* (2013.01); *G01N 33/566* (2013.01); *G01N 33/68* (2013.01); *G01N 2333/726* (2013.01)

(58) Field of Classification Search
None
See application file for complete search history.

(56) References Cited

U.S. PATENT DOCUMENTS

| | | |
|---|---|---|
| 2007/0009989 A1 | 1/2007 | Steinkuhler et al. |
| 2011/0143385 A1 | 6/2011 | Bauer et al. |
| 2017/0112773 A1 | 4/2017 | Stachowiak et al. |
| 2020/0181677 A1 | 6/2020 | Sivaramakrishnan et al. |

FOREIGN PATENT DOCUMENTS

WO    WO 2013/067173    5/2013

OTHER PUBLICATIONS

Kim et al., β2-adrenoceptor ligand efficacy is tuned by a two-stage interaction with the Gαs C terminus. PNAS 2021 vol. 118 No. 11 e2017201118, pp. 1-11.*
Adams, "Kinetic and Catalytic Mechanisms of Protein Kinases," Chem. Rev. 101(8):2271-2290, Jul. 7, 2001.
Alford et al., "The Rosetta All-atom Energy Function for Macromolecular Modeling and Design," J Chem. Theor. Comput. 13(6):3031-3048, Apr. 21, 2017.
Altman et al., "Precise Positioning of Myosin VI on Endocytic Vesicles In Vivo," PLoS Biol. 5(8)e210:1712-1722, Aug. 7, 2007.
Autry et al., "Nucleotide Activation of the Ca-ATPase," J Biol. Chem. 287(46):39070-39082, Nov. 9, 2012.
Baker, "The Selectivity of β-adrenoceptor Agonists at Human β1-, β2- and β3-adrenoceptors," Br. J Pharmacol. 160(5):1048-61, Jul. 2010.
Balaraman et al., "Folding of Small Proteins Using Constrained Molecular Dynamics," J. Phys. Chem. B: 115(23):7588-7596, May 18, 2011.
Beglov et al., "Finite Representation of an Infinite Bulk System: Solvent Boundary Potential for Computer Simulations," J Chem. Phys. 100(12):9050-9063, Jun. 15, 1994.
Brooks et al., "CHARMM: The Biomolecular Simulation Program," J. Comput. Chem. 30(10):1545-1614, Jul. 30, 2009.
Chan et al., "Model Membrane Systems and Their Applications," Curr. Opin. Chem. Biol, 11(6):581-587, Nov. 19, 2007.
Chan et al., "Signal Peptide Cleavage is Essential for Surface Expression of a Regulatory T Cell Surface Protein, Leucine Rich Repeat Containing 32 (LRRC32)," BMC Biochem 12(1):27, May 2011, 15 pages.
Darden et al., "Particle Mesh Ewald: An N•log(N) Method for Ewald Sums in Large Systems," J Chem. Phys. 98(12):10089-10092, Jun. 15, 1993.
De Oliveira et al., "Revisiting Protein Kinase-substrate Interactions: Toward Therapeutic Development," Science Signaling 9(420):re3, Mar. 22, 2016, 12 pages.
Del Piccolo et al., "Production of Plasma Membrane Vesicles with Chloride Salts and Their Utility as a Cell Membrane Mimetic for Biophysical Characterization of Membrane Protein Interactions," Anal. Chem. 84(20):8650-8655, Sep. 17, 2012.
Denis et al., "Probing Heterotrimeric G Protein Activation: Applications to Biased Ligands," Curr. Pharm. Des. 18(2)128-144, 2012.

(Continued)

*Primary Examiner* — Ruixiang Li
(74) *Attorney, Agent, or Firm* — Fish & Richardson P.C.

(57) ABSTRACT

The systems and methods described herein include the use of Giant Plasma Membrane Vesicles (GPMVs) derived from cells expressing SPASM sensors (e.g., SPASM GPCR sensors). Herein provided are giant plasma membrane vesicle (GPMV) sensors containing a membrane-associated polypeptide, where the membrane-associated polypeptide contains a target G protein-coupled receptor (GPCR), a linker including an amino acid sequence flanked by a FRET donor and a FRET acceptor, and a receptor partner for the target GPCR, where the linker separates the target GPCR from the receptor partner. In another aspect, provided is a method for quantifying the intrinsic efficacy of a compound for a target GPCR. In another aspect, provided is a method for identifying a compound that interacts with a target GPCR.

20 Claims, 13 Drawing Sheets
Specification includes a Sequence Listing.

(56) References Cited

OTHER PUBLICATIONS

Essmann et al., "A Smooth Particle Mesh Ewald Method," J Chem. Phys. 103(19):8577-8593, Nov. 15, 1995.
Gangupomu et al., "Mapping Conformational Dynamics of Proteins Using Torsional Dynamics Simulations," Biophys. J 104(9):1999-2008, May 7, 2013.
Gerlits et al., "Insights into the Phosphoryl Transfer Catalyzed by cAMP-dependent Protein Kinase: An X-ray Crystallographic Study of Complexes with Various Metals and Peptide Substrate SP20," Biochem. 52(21):3721-3727, May 1, 2013.
Gerlits et al., "Phosphoryl Transfer Reaction Snapshots in Crystals," J Biol. Chem. 290(25):15538-15548, Jun. 19, 2015.
Gregorio et al., "Single-molecule Analysis of Ligand Efficacy in β2AR-G-protein Activation," Nature 547(7661):68-73, Jun. 7, 2017.
Gupte et al., "Priming GPCR Signaling Through the Synergistic Effect of Two G Proteins," Proc. Natl. Acad. Sci. USA 114(14):3756-3761, Apr. 4, 2017.
Hanks et al., "The Eukaryotic Protein Kinase Superfamily: Kinase (Catalytic) Domain Structure and Classification," FASEB J. 9(8):576-596, May 1, 1995.
Harrison et al., "The [35S]GTPγS Binding Assay: Approaches and Applications in Pharmacology," Life Sci. 74(4):489-508, Dec. 2003.
Hess et al., "LINCS: A Linear Constraint Solver for Molecular Simulations," J Comput. Chem. 18(12):1463-1472, Sep. 1997.
Holowka et al., "Structural Studies on the Membrane-bound Immunoglobulin E-Receptor Complex. 1. Characterization of Large Plasma Membrane Vesicles from Rat Basophilic Leukemia Cells and Insertion of Amphipathic Fluorescent Probes," Biochemistry 22(14):3466-3474, Jul. 1983.
Hornbeck et al., "PhosphoSitePlus, 2014: Mutations, PTMs and Recalibrations," Nucleic Acids Res. 43:D512-520, Jan. 2015.
House et al., "Protein Kinase C Contains a Pseudosubstrate Prototope in Its Regulatory Domain," Science 238(4834):1726-1728, Dec. 1987.
Huang et al., "CHARMM36 All-atom Additive Protein Force Field: Validation Based on Comparison to NMR Data," J Comput. Chem. 34(25):2135-2145, Sep. 2013.
Jacobson et al., "A Hierarchical Approach to All-atom Protein Loop Prediction," Proteins Struct. Funct. Bioinf. 55(2):351-367, May 1, 2004.
Jain et al., "A Fast Recursive Algorithm for Molecular Dynamics Simulation," J Comput. Phys. 106(2):258-268, Jun. 1993.
Kenakin, "A Pharmacology Primer: Techniques for More Effective and Strategic Drug Discovery" 4th ed., Elsevier, San Diego, 2014, 431 pages.
Kim et al., "A cell-free FRET-based assay for profiling ligand efficacy for different GPCR ligands," Abstract and Poster, Presented at Proceedings of the 2017 GPCR Workshop, Kona, Hawaii, USA, Dec. 5-9, 2017, 3 pages.
Kim, "A Cell-Free FRET-based Assay for Profiling the Efficacy of Different GPCR Ligands," Presentation at the University of Minnesota Molecular, Cellular, Developmental Biology and Genetics Student Seminar, Minneapolis, Minnesota, USA, Mar. 29, 2018, 49 pages.
Kim, "A cell-free FRET-based assay for profiling the intrinsic efficacy of GPCR ligands," Abstract and Presentation, Presented at University of Minnesota Biophysics Seminar, Minneapolis, Minnesota, USA, Sep. 27, 2018, 32 pages.
Lakowicz, "Principles of Fluorescence Spectroscopy," 3rd ed., Springer, New York, 2006, 960 pages.
Larsen et al., "GneimoSim: A Modular Internal Coordinates Molecular Dynamics Simulation Package," J Comput. Chem. 35(31):2245-2255, Dec. 5, 2014.
Larsen et al., "Protein Structure Refinement of CASP Target Proteins Using GNEIMO Torsional Dynamics Method," Chem. Inf. Model. 54(2):508-517, Jan. 7, 2014.
Leonard et al., "Crystal Structure and Allosteric Activation of Protein Kinase C βII," Cell 144(1):55-66, Jan. 7, 2011.

Lopez-Sanchez et al., "Protein Kinase C-theta (PKCθ) Phosphorylates and Inhibits the Guanine Exchange Factor, GIV/Girdin," Proc. Natl. Acad. Sci. USA 110(14):5510-5515, Apr. 2, 2013.
Malik et al., "Detection of G Protein-selective G Protein-coupled Receptor (GPCR) Conformations in Live Cells," J. Biol. Chem. 288(24):17167-17178, Jun. 14, 2013.
Malik et al., "ER/K Linked GPCR-G Protein Fusions Systematically Modulate Second Messenger Response in Cells," Scientific Reports, 7(7749), Aug. 10, 2017, 13 pages.
Manning et al., "The Protein Kinase Complement of the Human Genome," Science 298(5600):1912-1934, Dec. 6, 2002.
Mochly-Rosen et al., "Protein Kinase C, An Elusive Therapeutic Target?," Nat. Rev. Drug Discov. 11(12):937-957, Dec. 2012.
Nishikawa et al., "Determination of the Specific Substrate Sequence Motifs of Protein Kinase C Isozymes," J Biol. Chem. 272(2):952-960, Jan. 10, 1997.
Park et al., "CASP 11 Refinement Experiments with ROSETTA," Proteins 84(S1):314-322, Sep. 2016.
Park et al., "Structure Refinement of Protein Low Resolution Models Using the GNEIMO Constrained Dynamics Method," J Phys. Chem. B. 116(8):2365-2375, Jan. 19, 2012.
PCT International Preliminary Report on Patentability in International Appln. No. PCT/US2018/036148, dated Dec. 10, 2019, 7 pages.
PCT International Preliminary Report on Patentability in International Appln. No. PCT/US2018/063827, dated Jun. 9, 2020, 7 pages.
PCT International Search Report and Written Opinion in International Appln. No. PCT/US2018/036148, dated Dec. 13, 2018, 11 pages.
PCT International Search Report and Written Opinion in International Appln. No. PCT/US2018/063827, dated Jun. 13, 2019, 11 pages.
Pearce et al., "The Nuts and Bolts of AGC Protein Kinases," Nat. Rev. Mol. Cell. Biol. 11(1):9-22, Jan. 2010.
Salazar et al., "Cardiac GPCRs: GPCR Signaling in Healthy and Failing Hearts," Biochim. Biophys. Acta—Biomembr. 1768(4):1006-1018, Apr. 2007.
Sarabipour et al., "Effect of the Achondroplasia Mutation on FGFR3 Dimerization and FGFR3 Structural Response to fgf1 and fgf2: A Quantitative FRET Study in Osmotically Derived Plasma Membrane Vesicles," Biochim. Biophys. Acta—Biomembr. 1858(7A):1436-1442, Jul. 2016.
Schulz et al., "Domain-specific Phosphomimetic Mutation Allows Dissection of Different Protein Kinase C (PKC) Isotype-triggered Activities of the RNA Binding Protein HuR," Cellular Signalling 25(12):2485-2495, Dec. 2013.
Semack et al., "G Protein-selective GPCR Conformations Measured Using FRET Sensors in a Live Cell Suspension Fluorometer Assay," J Vis. Exp. 115:e54696, Sep. 2016, 11 pages.
Semack et al., "Structural Elements in the Gαs and Gαq C Termini That Mediate Selective G Protein-coupled Receptor (GPCR) Signaling," J Biol. Chem. 291(34):17929-17940, Aug. 19, 2016.
Sezgin et al., "Elucidating Membrane Structure and Protein Behavior Using Giant Plasma Membrane Vesicles," Nat. Protoc. 7(6):1042-1051, May 2012.
Shepard et al., "A Cleavable N-Terminal Signal Peptide Promotes Widespread Olfactory Receptor Surface Expression in HEK293T Cells," PLoS One 8(7):e68758, Jul. 2013, 14 pages.
Sivaramakrishnan et al., "Systematic Control of Protein Interaction Using a Modular ER/K α-helix Linker," Proc. Natl. Acad. Sci. USA 108(51):20467-20472, Dec. 20, 2011.
Sivaramakrishnan, "Protein Engineering Approaches to Dissect Specificity in Cell Signaling," Presentation to R&D Systems, Minneapolis, Minnesota, USA, Jan. 13, 2017, 67 pages.
Sivaramakrishnan, "The kinase toolbox: Mapping protein interactions in cell signaling," Presented at Proceedings of the Gordon Research Conference on Phosphorylation and G-Protein Mediated Signaling Networks, Biddeford, Maine, USA, Jun. 5-10, 2016, 39 pages.
Sivaramakrishnan, "The subtle regulation of protein kinases: PKC self-assembly and substrate selectivity," Presentation at the Indian Institute for Stem Cell Science and Regenerative Medicine, Bangalore, India, Jul. 1, 2016, 60 pages.

(56) References Cited

OTHER PUBLICATIONS

Sivaramakrishnan, "The subtle regulation of protein kinases: PKC self-assembly and substrate selectivity," Presentation at the Indian Institute of Science, Bangalore, India, Jul. 14, 2016, 59 pages.
Smith et al., "ATP Competitive Protein Kinase C Inhibitors Demonstrate Distinct State-dependent Inhibition," PLoS One 6(10):e26338, Oct. 2011, 9 pages.
Sommese et al., "Substrate Affinity Differentially Influences Protein Kinase C Regulation and Inhibitor Potency," J Biol. Chem. 291(42):21963-21970, Oct. 14, 2016.
Sommese et al., "The Role of Regulatory Domains in Maintaining Autoinhibition in the Multidomain Kinase PKCα," J Biol. Chem. 292(7):2873-2880, Feb. 17, 2017.
Sommese, "Dissecting Cell Signaling Using Protein Engineering & DNA Nanotechnology," Presentation at the University of Pennsylvania School of Medicine, Philadelphia, Pennsylvania, USA, Jan. 24, 2017, 70 pages.
Sommese, "Dissecting Cell Signaling Using Protein Engineering & DNA Nanotechnology," Presentation at the Washington University School of Medicine in St. Louis, St. Louis, Missouri, USA, Jan. 31, 2017, 70 pages.
Sommese, "Dissecting Protein Function Using Protein Engineering & DNA Nanotechnology," Presentation at MilliporeSigma, Burlington, Massachusetts, USA, Feb. 10, 2017, 37 pages.
Sommese, "Dissecting Specificity in Kinase Signaling Using Protein Engineering," Presentation to the Pfizer Structural and Molecular Sciences Department, Groton, Connecticut, USA, Jan. 27, 2017, 59 pages.
Sommese, "Tuning the Substrate-Kinase Interaction in PKCα," Abstract and Presentation, Presented at Proceedings of the Gordon Research Seminar on Phosphorylation and G-Protein Mediated Signaling Networks, Biddeford, Maine, USA, Jun. 4-5, 2016, 38 pages.
Sommese, "Tuning the Substrate-Kinase Interaction in PKCα," Presentation at Life Sciences Research Foundation 2016 Meeting, Seattle, Washington, USA, Oct. 15, 2016, 28 pages.
Sugita et al., "Replica-exchange Molecular Dynamics Method for Protein Folding," Chem. Phys. Lett. 314(1):141-151, Nov. 26, 1999.
Swanson et al., "Conserved Modular Domains Team up to Latch-open Active Protein Kinase Cα," J Biol. Chem. 289(25): 17812-17829, Jun. 20, 2014.
Taylor et al., "Dynamics of Signaling by PKA," Biochim. Biophys. Acta. 1754:25-37, Sep. 22, 2005.
Taylor et al., "Protein Kinases: Evolution of Dynamic Regulatory Proteins," Trends Biochem. Sci. 36(2):65-77, Feb. 2011.
Toropova et al., "Lis1 Regulates Dynein by Sterically Blocking its Mechanochemical Cycle," eLife 2014(3):e03372, retrieved on Aug. 5, 2020, retrieved at URL<https://elifesciences.org/articles/03372>, Nov. 7, 2014, 72 pages.
Tyndall et al., "GPCR Agonists and Antagonists in the Clinic," Med Chem. 1(4):405-421, Jun. 1, 2005.
Ubersax et al., "Mechanisms of Specificity in Protein Phosphorylation," Nature Rev. Mol. Cell. Biol. 8(7):530-541, Jul. 2007.
Vaidehi et al., "Constant Temperature Constrained Molecular Dynamics: The Newton-Euler Inverse Mass Operator Method," J Phys. Chem. 100(25):10508-10517, Jun. 20, 1996.
Van Der Spoel et al., "GROMACS: Fast, Flexible, and Free," J Comput. Chem. 26(16):1701-1718, Dec. 2005.
Verma et al., "The Tumour Suppressor RASSF1A is a Novel Substrate of PKC," FEBS Lett. 582(15):2270-2276, Jun. 2, 2008.
Wagner et al., "Advanced Techniques for Constrained Internal Coordinate Molecular Dynamics," J Comput. Chem. 34(11):904-914, Apr. 30, 2013.
Webb et al., "Comparative Protein Structure Modeling Using MODELLER," Curr. Protoc. Bioinforma. 47:5.6.1-32, Sep. 8, 2014.
Yang et al., "Crystal Structure of an Activated Akt/Protein Kinase B Ternary Complex with GSK3-peptide and AMP-PNP," Nat. Struct. Biol. 9(12):940-944, Dec. 2002.

Ye et al., "Mechanistic Insights into Allosteric Regulation of the A2A Adenosine G Protein-coupled Receptor by Physiological Cations," Nat. Commun. 9(1):1372, Apr. 2018, 13 pages.
UniProt Database Accession No. P17252, May 2016, 14 pages (Year: 2016).
Ritt et al., "Visualizing and Manipulating Focal Adhesion Kinase Regulation in Live Cells," J. Biol. Chem. 288:8875-8886, 2013.
U.S. Appl. No. 16/619,798, filed Dec. 5, 2019, Sivaraj Sivaramakrishnan, Published as US 2020/0181677.
Ahn et al., "Interaction of the human insulin receptor tyrosine kinase from the baculovirus expression system with protein kinase C in a cell-free system," J. Biol. Chem., Apr. 1993, 268(10):7571-7576.
Ali et al., "Exploitation of protein kinase C: A useful target for cancer therapy," Cancer Treat. Rev., Feb. 2009, 35(1):1-8.
Amess et al., "Multisite phosphorylation of the 80 kDa (MARCKS) protein kinase C substrate in C3H/10T1/2 fibroblasts. Quantitative analysis of individual sites by solid-phase microsequencing," FEBS Lett., Feb. 1992, 297(3):285-291.
Anilkumar et al., "Interaction of fascin and protein kinase Calpha: a novel intersection in cell adhesion and motility," EMBO J., Oct. 2003, 22(20):5390-5402.
Antal et al., "Cancer-Associated Protein Kinase C Mutations Reveal Kinase's Role as Tumor Suppressor," Cell, Jan. 2015, 160(3):489-502.
Ayala et al., "An efficient protocol for the complete incorporation of methyl-protonated alanine in perdeuterated protein," J. Biomol. NMR, Feb. 2009, 43(2):111-119.
Barouch-Bentov et al., "Mechanisms of drug resistance in kinases," Expert Opin. Investig. Drugs, Feb. 2011, 20(2):153-208.
Battiste et al., "Utilization of Site-Directed Spin Labeling and High-Resolution Heteronuclear Nuclear Magnetic Resonance for Global Fold Determination of Large Proteins with Limited Nuclear Overhauser Effect Data," Biochemistry, May 2000, 39(18):5355-5365.
Bauman et al., "Kinase- and phosphatase-anchoring proteins: harnessing the dynamic duo," Nat. Cell Biol., Aug. 2002, 4(8):E203-E206.
Bhattacharya et al., "Conserved Mechanism of Conformational Stability and Dynamics in G-Protein-Coupled Receptors," J. Chem. Theory Comput., Nov. 2016, 12(11):5575-5584.
Bhattacharya et al., "Differences in Allosteric Communication Pipelines in the Inactive and Active States of a GPCR," Biophys. J., Jul. 2014, 107(2):422-434.
Blackshear et al., "The MARCKS family of cellular protein kinase C substrates," J. Biol. Chem., 1993, 268:1501-1504.
Blume-Jensen et al., "Increased Kit/SCF receptor induced mitogenicity but abolished cell motility after inhibition of protein kinase C," EMBO J., Nov. 1993, 12(11):4199-4209.
Bosco et al., "Fine tuning of protein kinase C (PKC) isoforms in cancer: shortening the distance from the laboratory to the bedside," Mini Rev. Med. Chem., Mar. 2011, 11(3):185-199.
Cembran et al., "Conformational equilibrium of N-myristoylated cAMP-dependent protein kinase A by molecular dynamics simulations," Biochemistry, Dec. 2012, 51(51):10186-10196.
Cembran et al., "NMR mapping of protein conformational landscapes using coordinated behavior of chemical shifts upon ligand binding," Phys. Chem. Chem. Phys., Apr. 2014, 16(14):6508-6518.
Chambers et al., "Identification of specific sites in human P-glycoprotein phosphorylated by protein kinase C," J. Biol. Chem., Mar. 1993, 268(7):4592-4595.
Chao et al., "FLAMEnGO 2.0: an enhanced fuzzy logic algorithm for structure-based assignment of methyl group resonances," J. Magn. Reson., Aug. 2014, 245:17-23.
Chao et al., "FLAMEnGO: a fuzzy logic approach for methyl group assignment using NOESY and paramagnetic relaxation enhancement data," J. Magn. Reson., Jan. 2012, 214:103-110.
Chen et al., "Elevated MARCKS phosphorylation contributes to unresponsiveness of breast cancer to paclitaxel treatment," Oncotarget, Jun. 2015, 6(17):15194-15208.
Chen et al., "Identification of novel, potent and selective inhibitors of Polo-like kinase 1," Bioorg. Med. Chem. Lett., Jan. 2012, 22(2):1247-1250.

(56) References Cited

OTHER PUBLICATIONS

Clarke et al., Multidrug resistance/P-glycoprotein and breast cancer: review and meta-analysis. Semin. Oncol., Dec. 2005, 32(6 Suppl. 7):S9-S15.
Clore et al., "Four-dimensional 13C/13C-edited nuclear Overhauser enhancement spectroscopy of a protein in solution: application to interleukin 1 beta," Biochemistry, Jan. 1991, 30(1):12-18.
Clore et al., "Theory, practice, and applications of paramagnetic relaxation enhancement for the characterization of transient low-population states of biological macromolecules and their complexes," Chem. Rev., Sep. 2009, 109(9):4108-4139.
Conklin et al., "Substitution of three amino acids switches receptor specificity of Gqα to that of Giα," Nature, May 1993, 363:274-276.
Cook et al., "Adenosine cyclic 3',5'-monophosphate dependent protein kinase: kinetic mechanism for the bovine skeletal muscle catalytic subunit," Biochemistry, Nov. 1982, 21(23):5794-5799.
Corbit et al., "Activation of Raf-1 signaling by protein kinase C through a mechanism involving Raf kinase inhibitory protein," J. Biol. Chem., Apr. 2003, 278(15):13061-13068.
Dekker et al., "Altered substrate selectivity of PKC-eta pseudosubstrate site mutants," FEBS Lett., Aug. 1993, 329(1-2):129-133.
Dekker et al., "Mutagenesis of the regulatory domain of rat protein kinase C-eta. A molecular basis for restricted histone kinase activity," J. Biol. Chem., Sep. 1993, 268(26):19498-19504.
Deloulme et al., "Neuromodulin (GAP43): a neuronal protein kinase C substrate is also present in 0-2A glial cell lineage. Characterization of neuromodulin in secondary cultures of oligodendrocytes and comparison with the neuronal antigen," J. Cell Biol., Oct. 1990, 111(4):1559-1569.
Dempsey et al., "Protein kinase C isozymes and the regulation of diverse cell responses," Am. J. Physiol. Lung Cell. Mol. Physiol., Sep. 2000, 279(3):L429-L438.
Endicott et al., "The structural basis for control of eukaryotic protein kinases," Annu. Rev. Biochem., Jul. 2012, 81:587-613.
Evenou et al., "The potent protein kinase C-selective inhibitor AEB071 (sotrastaurin) represents a new class of immunosuppressive agents affecting early T-cell activation," J. Pharmacol. Exp. Ther., Sep. 2009, 330(3):792-801.
Fabbro et al., "Inhibitors of protein kinases: CGP 41251, a protein kinase inhibitor with potential as an anticancer agent," Pharmacol. Ther., May-Jun. 1999, 82(2-3):293-301.
Fabre et al., "Protein kinase C inhibitors; structure-activity relationships in K252c-related compounds," Bioorg. Med. Chem., Sep. 1993, 1(3):193-196.
Foda et al., "A dynamically coupled allosteric network underlies binding cooperativity in Src kinase," Nat. Commun., Jan. 2015, 6:5939.
Fuxreiter et al., "Local structural disorder imparts plasticity on linear motifs," Bioinformatics, Apr. 2007, 23(8):950-956.
Gaffarogullari et al., "A myristoyl/phosphoserine switch controls cAMP-dependent protein kinase association to membranes," J. Mol. Biol., Aug. 2011, 411(4)823-836.
Gardner et al., "Production and Incorporation of 15N, 13C, 2H (1H-δ1 Methyl) Isoleucine into Proteins for Multidimensional NMR Studies," J. Am. Chem. Soc., Aug. 1997, 119(32):7599-7600.
Gong et al., "The C2 Domain and Altered ATP-Binding Loop Phosphorylation at Ser Mediate the Redox-Dependent Increase in Protein Kinase C-δ Activity," Mol. Cell. Biol., May 2015, 35(10):1727-1740.
Goto et al., "A robust and cost-effective method for the production of Val, Leu, Ile (delta 1) methyl-protonated 15N-, 13C-, 2H-labeled proteins," J. Biomol. NMR, Apr. 1999, 13(4):369-74.
Graff et al., "The Protein Kinase Cβ-Selective Inhibitor, Enzastaurin (LY317615.HC1), Suppresses Signaling through the AKT Pathway, Induces Apoptosis, and Suppresses Growth of Human Colon Cancer and Glioblastoma Xenografts," Cancer Res., Aug. 2005, 65(16):7462-7469.
Gwak et al., "Protein-kinase-C-mediated beta-catenin phosphorylation negatively regulates the Wnt/beta-catenin pathway," J. Cell Sci., Nov. 2006, 119(Pt. 22):4702-4709.

Hamm et al., "Site of G Protein Binding to Rhodopsin Mapped with Synthetic Peptides from the α Subunit," Science, Aug. 1988, 241(4867):832-835.
Han et al., "Allosteric communication between protomers of dopamine class A GPCR dimers modulates activation," Nature Chem. Biol., Aug. 2009, 5:688-695.
Hexner et al., "Lestaurtinib (CEP701) is a JAK2 inhibitor that suppresses JAK2/STAT5 signaling and the proliferation of primary erythroid cells from patients with myeloproliferative disorders," Blood, Jun. 2008, 111(12):5663-5671.
Hirschi et al., "An overlapping kinase and phosphatase docking site regulates activity of the retinoblastoma protein," Nat. Struct. Mol. Biol., Sep. 2010, 17(9):1051-1057.
Hutti et al., "A rapid method for determining protein kinase phosphorylation specificity," Nat. Methods, Oct. 2004, 1(1):27-29.
Iakoucheva et al., "The importance of intrinsic disorder for protein phosphorylation," Nucleic Acids Res., Feb. 2004, 32(3):1037-1049.
Ikura et al., "Detection of nuclear Overhauser effects between degenerate amide proton resonances by heteronuclear three-dimensional NMR spectroscopy," J. Am. Chem. Soc., Nov. 1990, 112(24):9020-9022.
Jiang et al., "Inhibition of Chk1 by the G2 DNA damage checkpoint inhibitor isogranulatimide," Mol. Cancer Ther., Oct. 2004, 3(10):1221-1227.
Jirousek et al., "(S)-13-[(dimethylamino)methyl]-10,11,14,15-tetrahydro-4,9:16, 21-dimetheno-1H, 13H-dibenzo[e,k]pyrrolo[3,4-h][1,4,13]oxadiazacyclohexadecene-1,3(2H)-dione (LY333531) and related analogues: isozyme selective inhibitors of protein kinase C beta," J. Med. Chem., Jul. 1996, 39(14):2664-2671.
Johnson et al., "Kinomics: methods for deciphering the kinome," Nat. Methods, Jan. 2005, 2(1):17-25.
Kandel et al., "Overcoming potential energy distortions in constrained internal coordinate molecular dynamics simulations," J. Chem. Phys., Jan. 2016, 144(4):44112.
Keller et al., "The role of Raf kinase inhibitor protein (RKIP) in health and disease," Biochem. Pharmacol., Sep. 2004, 68(6):1049-1053.
Kemp et al., "Protein kinase recognition sequence motifs," Trends Biochem. Sci., Sep. 1990, 15(9):342-346.
Kim et al., "A Semiautomated Assignment Protocol for Methyl Group Side Chains in Large Proteins," Methods Enzymol., 2016, 566:35-57.
Kim et al., "Dysfunctional conformational dynamics of protein kinase A induced by a lethal mutant of phospholamban hinder phosphorylation," Proc. Natl. Acad. Sci. USA., Mar. 2015, 112(12):3716-3721.
Kim et al., "Identification of anti-malarial compounds as novel antagonists to chemokine receptor CXCR4 in pancreatic cancer cells," PLoS One, Feb. 2012, 7(2):e31004.
Kim et al., "Substrate competition as a source of ultrasensitivity in the inactivation of Weel," Cell, Mar. 2007, 128(6):1133-1145.
Kim et al., "Uncoupling Catalytic and Binding Functions in the Cyclic AMP-Dependent Protein Kinase A," Structure, Mar. 2016, 24(3):353-363.
Kishimoto et al., "Studies on the phosphorylation of myelin basic protein by protein kinase C and adenosine 3':5'-monophosphate-dependent protein kinase," J. Biol. Chem., Oct. 1985, 260(23):12492-12499.
Leavitt et al., "Direct measurement of protein binding energetics by isothermal titration calorimetry," Curr. Opin. Struct. Biol., Oct. 2001, 11(5):560-566.
Lee et al., "CCR9-mediated signaling through β-catenin and identification of a novel CCR9 antagonist," Mol. Oncol., Oct. 2015, 9(8):1599-1611.
Lennartsson et al., "Stem cell factor receptor/c-Kit: from basic science to clinical implications," Physiol. Rev., Oct. 2012, 92(4):1619-1649.
Li et al., "Computational method to identify druggable binding sites that target protein-protein interactions," J. Chem. Inf. Model., May 2014, 54(5):1391-400.
Li et al., "Mapping the Hydrogen Bond Networks in the Catalytic Subunit of Protein Kinase A Using H/D Fractionation Factors," Biochemistry, Jul. 2015, 54(26):4042-4049.

(56) References Cited

OTHER PUBLICATIONS

Liu et al., "Rational design of inhibitors that bind to inactive kinase conformations," Nat. Chem. Biol., Jul. 2006, 2(7):358-364.

Manoukian et al., "Role of glycogen synthase kinase-3 in cancer: regulation by Wnts and other signaling pathways," Adv. Cancer Res., 2002, 84:203-229.

Maroney et al., "Motoneuron apoptosis is blocked by CEP-1347 (KT 7515), a novel inhibitor of the JNK signaling pathway," J. Neurosci., Jan. 1998, 18(1):104-111.

Martiny-Baron et al., "Selective inhibition of protein kinase C isozymes by the indolocarbazole Gö 6976," J. Biol. Chem., May 1993, 268(13):9194-9197.

Masterson et al., "Allosteric cooperativity in protein kinase A," Proc. Natl. Acad. Sci., Jan. 2008, 105(2):506-511.

Masterson et al., "Allostery and binding cooperativity of the catalytic subunit of protein kinase A by NMR spectroscopy and molecular dynamics simulations," Adv. Protein Chem. Struct. Biol., 2012, 87:363-389.

Masterson et al., "Dynamically committed, uncommitted, and quenched states encoded in protein kinase A revealed by NMR spectroscopy," Proc. Natl. Acad. Sci. USA., Apr. 2011, 108(17):6969-6974.

Masterson et al., "Dynamics connect substrate recognition to catalysis in protein kinase A," Nat. Chem. Biol., Nov. 2010, 6(11):821-828.

Meng et al., "MAP4K family kinases act in parallel to MST1/2 to activate LATS1/2 in the Hippo pathway," Nat. Commun., Oct. 2015, 6:8357.

Michie et al., "The link between PKCalpha regulation and cellular transformation," Immunol. Lett., Jan. 2005, 96(2):155-162.

Moore et al., "Dual regulation of glycogen synthase kinase 3 (GSK3)α/β by protein kinase C (PKC)α and Akt promotes thrombin-mediated integrin αIIbβ3 activation and granule secretion in platelets," J. Biol. Chem., Feb. 2013, 288(6):3918-3928.

Morin, "beta-catenin signaling and cancer," Bioessays, Dec. 1999, 21(12):1021-1030.

Moss et al., "Identification of the cAMP-dependent protein kinase and protein kinase C phosphorylation sites within the major intracellular domains of the beta 1, gamma 2S, and gamma 2L subunits of the gamma-aminobutyric acid type A receptor," J. Biol. Chem., Jul. 1992, 267(20):14470-14476.

Muller et al., "p53 mutations in cancer," Nat. Cell Biol., Jan. 2013, 15(1):2-8.

Nedjai et al., "CXCR3 antagonist VUF10085 binds to an intrahelical site distinct from that of the broad spectrum antagonist TAK-779," Br. J. Pharmacol., 172, 1822-33 (2015).

Neman et al., "Human breast cancer metastases to the brain display GABAergic properties in the neural niche," Proc. Natl. Acad. Sci. USA., 111, 984-9 (2014).

Newton, "Protein kinase C: structure, function, and regulation," J. Biol. Chem., Dec. 1995, 270(48):28495-28498.

Noland Jr. et al., "Protein kinase C phosphorylation of cardiac troponin I and troponin T inhibits Ca(2+)-stimulated MgATPase activity in reconstituted actomyosin and isolated myofibrils, and decreases actin-myosin interactions," J. Mol. Cell Cardiol., Jan. 1993, 25(1):53-65.

Normanno et al., "Epidermal growth factor receptor (EGFR) signaling in cancer," Gene, Jan. 2006, 366(1):2-16.

Norris et al., "A method for multiprotein assembly in cells reveals independent action of kinesins in complex," J. Cell. Biol., Nov. 2014, 207(3):393-406.

Obata et al., "Peptide and protein library screening defines optimal substrate motifs for AKT/PKB," J. Biol. Chem., Nov. 2000, 275(46):36108-36115.

Osada et al., "A new inhibitor of protein kinase C, RK-1409 (7-oxostaurosporine). I. Taxonomy and biological activity," J. Antbiot., Feb. 1992, 45(2):189-194.

Pervushin et al., "Attenuated T2 relaxation by mutual cancellation of dipole-dipole coupling and chemical shift anisotropy indicates an avenue to NMR structures of very large biological macromolecules in solution," Proc. Natl. Acad. Sci. USA, Nov. 1997, 94(23):12366-12371.

Pollack et al., "Inhibition of epidermal growth factor receptor-associated tyrosine phosphorylation in human carcinomas with CP-358,774: dynamics of receptor inhibition in situ and antitumor effects in athymic mice," J. Pharmacol. Exp. Ther., Nov. 1999, 291(2):739-748.

Raab et al., "Targeting PKC: a novel role for beta-catenin in ER stress and apoptotic signaling," Blood, Feb. 2009, 113(7):1513-1521.

Rasmussen et al., "Crystal structure of the β2 adrenergic receptor-Gs protein complex," Nature, Jul. 2011, 477:549-555.

Reyland, "Protein kinase C isoforms: Multi-functional regulators of cell life and death," Front. Biosci. (Landmark Ed)., Jan. 2009, 14(6):2386-2399.

Ritt et al., "Correlation between Activity and Domain Complementation in Adenylyl Cyclase Demonstrated with a Novel Fluorescence Resonance Energy Transfer Sensor," Mol. Pharmacol., Apr. 2016, 89(4):407-412.

Rossy et al., "Conformational states of the kinase Lck regulate clustering in early T cell signaling," Nature Immunol., Dec. 2012, 14:82-89.

Rust et al., "Kinase Consensus Sequences: A Breeding Ground for Crosstalk," ACS Chem. Biol., Sep. 2011, 6(9):881-892.

Ruvolo et al., "A functional role for mitochondrial protein kinase Calpha in Bcl2 phosphorylation and suppression of apoptosis," J. Biol. Chem., Sep. 1998, 273(39):25436-25442.

Saio et al., "Structural Basis for Protein Antiaggregation Activity of the Trigger Factor Chaperone," Science, May 2014, 344(6184):1250494-1250494.

Salzmann et al., "TROSY in triple-resonance experiments: new perspectives for sequential NMR assignment of large proteins," Proc. Natl. Acad. Sci. USA, Nov. 1998, 95(23):13585-13590.

Schafer et al., "Decay of an active GPCR: Conformational dynamics govern agonist rebinding and persistence of an active, yet empty, receptor state," Proc. Natl. Acad. Sci. USA, Oct. 2016, 113(42):11961-11966.

Selvaratnam et al., "Mapping allostery through the covariance analysis of NMR chemical shifts," Proc. Natl. Acad. Sci. USA, Apr. 2011, 108(15):6133-6138.

Selvaratnam et al., "The auto-inhibitory role of the EPAC hinge helix as mapped by NMR," PLoS One, Nov. 2012, 7(11):e48707.

Shaffer et al., "Detection of conformational changes along the kinetic pathway of protein kinase A using a catalytic trapping technique," Biochemistry, Sep. 1999, 38(37):12072-12079.

Sim et al., "Targeting of PKA, PKC and protein phosphatases to cellular microdomains," Cell Calcium, Nov. 1999, 26(5):209-217.

Sivaramakrishnan et al., "Combining single-molecule optical trapping and small-angle x-ray scattering measurements to compute the persistence length of a protein ER/K alpha-helix," Biophys. J., Dec. 2009, 97(11):2993-2999.

Sivaramakrishnan et al., "Dynamic charge interactions create surprising rigidity in the ER/K alpha-helical protein motif," Proc. Natl. Acad. Dci. USA, Sep. 2008, 105(36):13356-13361.

Songyang et al., "Use of an oriented peptide library to determine the optimal substrates of protein kinases," Curr. Biol., Nov. 1994, 4(11):973-982.

Srivastava et al., "Synchronous opening and closing motions are essential for cAMP-dependent protein kinase A signaling," Structure, Dec. 2014, 22(12):1735-1743.

Steinberg, "Structural Basis of Protein Kinase C Isoform Function," Physiol. Rev., Oct. 2008, 88(4):1341-1378.

Stewart et al., "Protein kinase C-α mediates epidermal growth factor receptor transactivation in human prostate cancer cells," Mol. Cancer Ther., May 2005, 4(5):726-732.

Swanson et al., "Calcium Stimulates Self-Assembly of Protein Kinase C α In Vitro," PLoS One, Oct. 2016, 11(10):e0162331, 21 pages.

Swanson et al., "Harnessing the unique structural properties of isolated α-helices," J. Biol. Chem., Sep. 2014, 289(37):25460-25467.

(56) References Cited

OTHER PUBLICATIONS

Tamaoki et al., "Staurosporine, a potent inhibitor of phospholipid/Ca++dependent protein kinase," Biochem. Biophys. Res. Commun., Mar. 1986, 135(2):397-402.

Taylor et al., "Assembly of allosteric macromolecular switches: lessons from PKA," Nat. Rev. Mol. Cell Biol., Oct. 2012, 13(10):646-658.

Taylor et al., "PKA: a portrait of protein kinase dynamics," Biochim. Biophys. Acta, Mar. 2004, 1697(1-2):259-269.

Thoma et al., "Identification of a potent Janus kinase 3 inhibitor with high selectivity within the Janus kinase family," J. Med. Chem., Jan. 2011, 54(1):284-288.

Thomsen et al., "GPCR-G Protein-β-Arrestin Super-Complex Mediates Sustained G Protein Signaling," Cell, Aug. 2016, 166(4):907-919.

Tonelli et al., "Carbonyl carbon label selective (CCLS) 1H-15N HSQC experiment for improved detection of backbone 13C-15N cross peaks in larger proteins," J. Biomol. NMR, Nov. 2007, 39(3):177-185.

Toton et al., "Protein kinase Cε as a cancer marker and target for anticancer therapy," 2011, Pharmacol. Rep., 63(1):19-29.

Toullec et al., "The bisindolylmaleimide GF 109203X is a potent and selective inhibitor of protein kinase C," J. Biol. Chem., Aug. 1991, 266(24):15771-15781.

Tugarinov et al., "Ile, Leu, and Val methyl assignments of the 723-residue malate synthase G using a new labeling strategy and novel NMR methods," J. Am. Chem. Soc., Nov. 2003, 125(45):13868-13878.

Vaidehi et al., "Allosteric communication pipelines in G-protein-coupled receptors," Curr. Opin. Pharmacol., Oct. 2016, 30:76-83.

Vaidehi et al., "Internal coordinate molecular dynamics: a foundation for multiscale dynamics," J. Phys. Chem. B, Jan. 2015, 119(4):1233-1242.

Veglia et al., "Role of conformational entropy in the activity and regulation of the catalytic subunit of protein kinase A," FEBS J., Aug. 2013, 280:5608-5615.

Velyvis et al., "An economical method for production of (2)H,(13)CH3-threonine for solution NMR studies of large protein complexes: application to the 670 kDa proteasome," PLoS One, Sep. 2012, 7(9):e43725.

Vigneri et al., "Insulin, insulin receptors, and cancer," J. Endocrinol. Invest., Dec. 2016, 39(12):1365-1376.

Wilkinson et al., "Isoenzyme specificity of bisindolylmaleimides, selective inhibitors of protein kinase C," Biochem. J., Sep. 1993, 294(Pt. 2):335-337.

Woods et al., "Protein kinase C involvement in focal adhesion formation," J. Cell Sci., Feb. 1992, 101(Pt. 2):277-290.

Xing et al., "Fascin, an actin-bundling protein, promotes breast cancer progression in vitro," Cell Biochem. Funct., Jun. 2011, 29(4):303-310.

Youle et al., "The BCL-2 protein family: opposing activities that mediate cell death," Nat. Rev. Mol. Cell Biol., Jan. 2008, 9(1):47-59.

Youmell et al., "Regulation of the p53 protein by protein kinase C alpha and protein kinase C zeta," Biochem. Biophys. Res. Commun., Apr. 1998, 245(2):514-518.

Young et al., "GABA's control of stem and cancer cell proliferation in adult neural and peripheral niches," Physiology, Jun. 2009, 24:171-185.

Yu et al., "Stereoselective synthesis, biological evaluation, and modeling of novel bile acid-derived G-protein coupled bile acid receptor 1 (GP-BAR1, TGR5) agonists," Bioorg. Med. Chem., Apr. 2015, 23(7):1613-1628.

Zaidel-Bar et al., "Functional atlas of the integrin adhesome," Nature Cell Biol., Aug. 2007, 9:858-867.

Zhang et al., "Targeting cancer with small molecule kinase inhibitors," Nat. Rev. Cancer, Jan. 2009, 9(1):28-39.

Zhou et al., "Participation of ADP dissociation in the rate-determining step in cAMP-dependent protein kinase," Biochemistry, Dec. 1997, 36(50):15733-15738.

\* cited by examiner

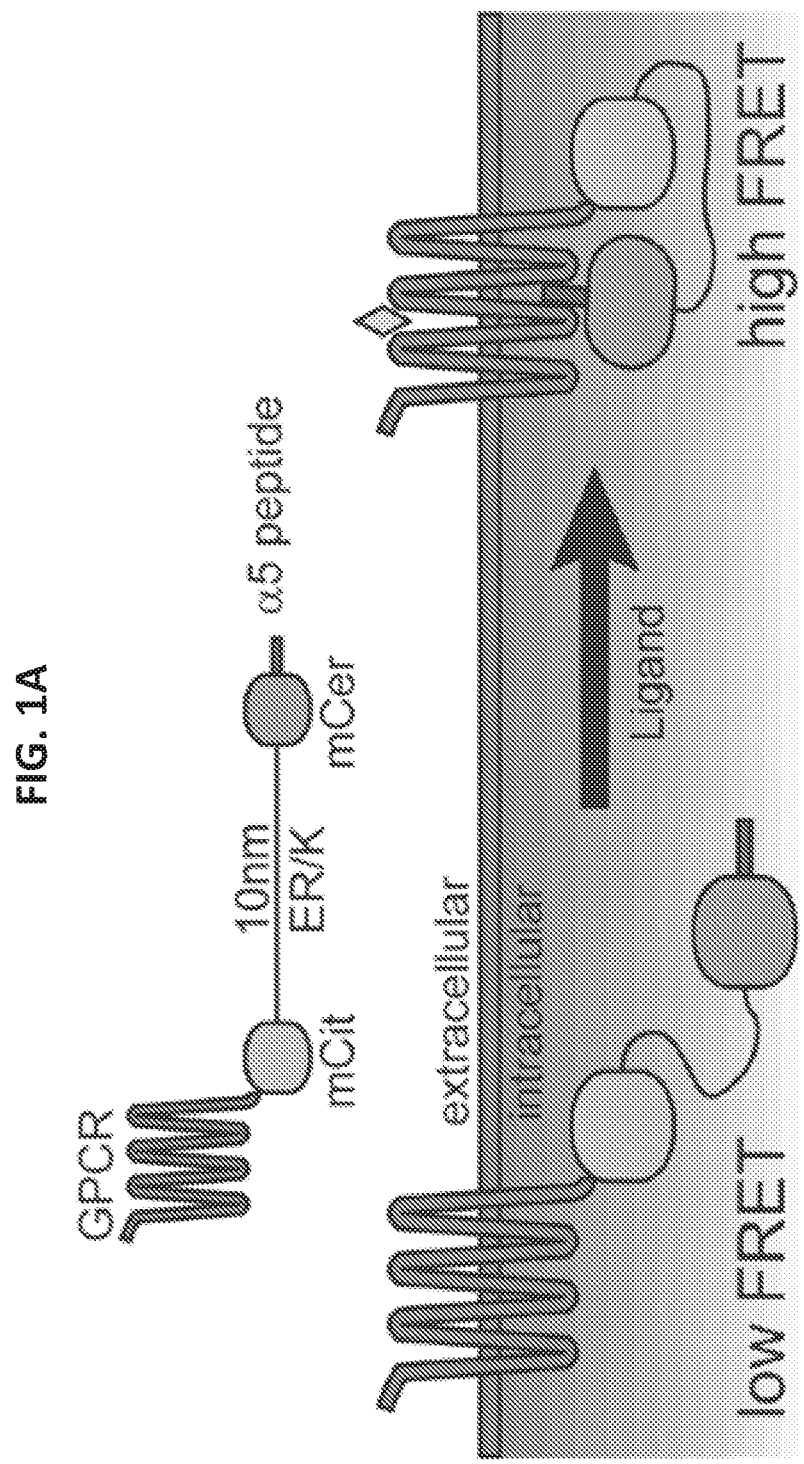

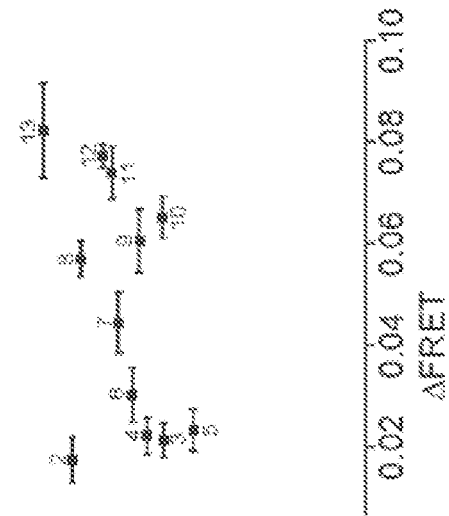
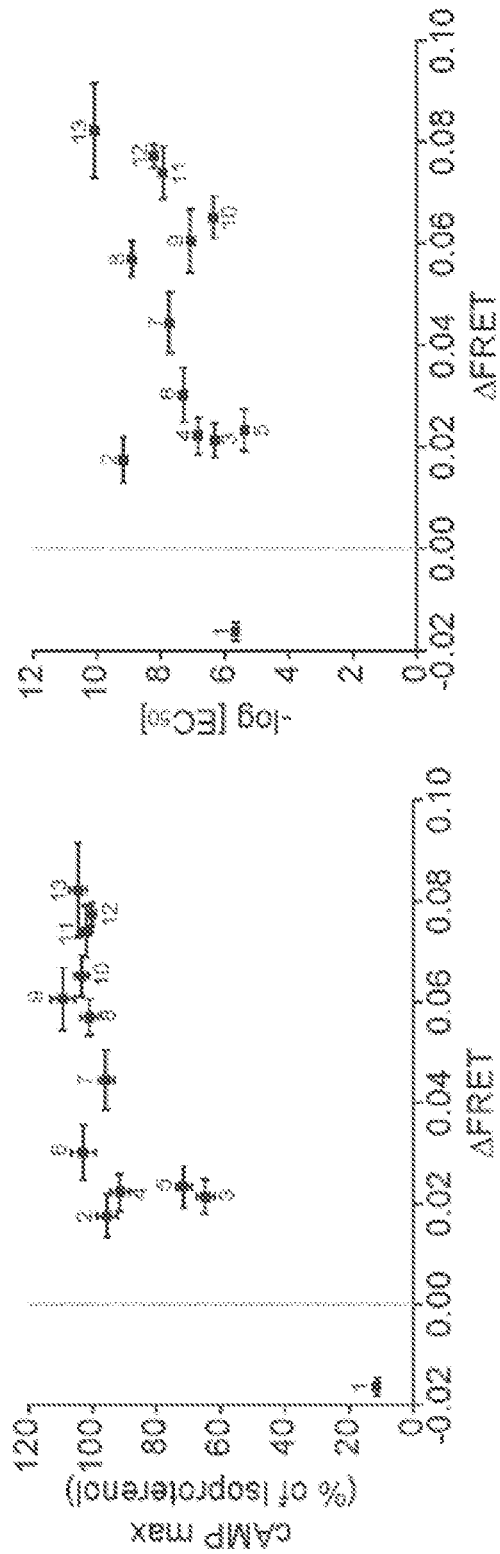
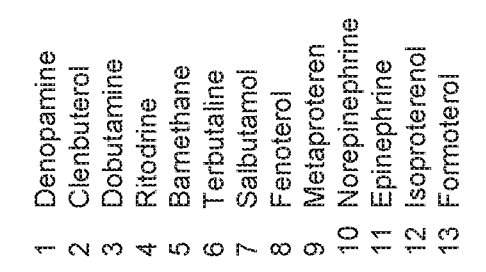
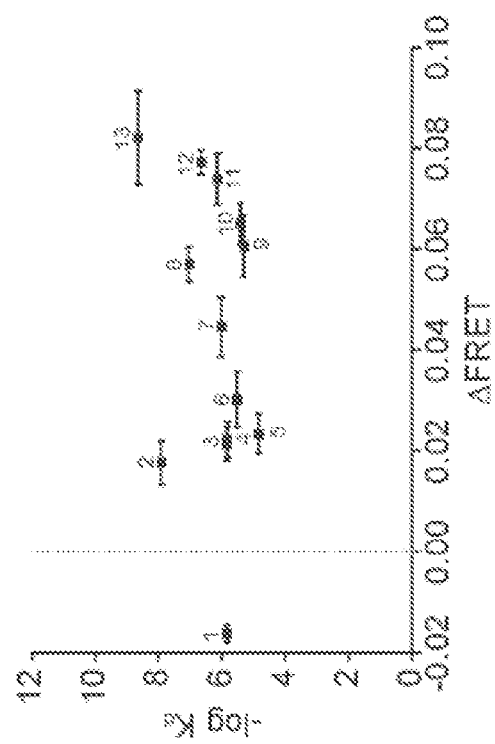

```
                              SEQUENCE LISTING

<160> NUMBER OF SEQ ID NOS: 10

<210> SEQ ID NO 1
<211> LENGTH: 413
<212> TYPE: PRT
<213> ORGANISM: Homo sapiens

<400> SEQUENCE: 1

Met Gly Gln Pro Gly Asn Gly Ser Ala Phe Leu Leu Ala Pro Asn Arg
1               5                   10                  15

Ser His Ala Pro Asp His Asp Val Thr Gln Gln Arg Asp Glu Val Trp
            20                  25                  30

Val Val Gly Met Gly Ile Val Met Ser Leu Ile Val Leu Ala Ile Val
        35                  40                  45

Phe Gly Asn Val Leu Val Ile Thr Ala Ile Ala Lys Phe Glu Arg Leu
    50                  55                  60

Gln Thr Val Thr Asn Tyr Phe Ile Thr Ser Leu Ala Cys Ala Asp Leu
65                  70                  75                  80

Val Met Gly Leu Ala Val Val Pro Phe Gly Ala Ala His Ile Leu Met
                85                  90                  95

Lys Met Trp Thr Phe Gly Asn Phe Trp Cys Glu Phe Trp Thr Ser Ile
            100                 105                 110

Asp Val Leu Cys Val Thr Ala Ser Ile Glu Thr Leu Cys Val Ile Ala
        115                 120                 125

Val Asp Arg Tyr Phe Ala Ile Thr Ser Pro Phe Lys Tyr Gln Ser Leu
    130                 135                 140

Leu Thr Lys Asn Lys Ala Arg Val Ile Ile Leu Met Val Trp Ile Val
145                 150                 155                 160

Ser Gly Leu Thr Ser Phe Leu Pro Ile Gln Met His Trp Tyr Arg Ala
                165                 170                 175

Thr His Gln Glu Ala Ile Asn Cys Tyr Ala Asn Glu Thr Cys Cys Asp
            180                 185                 190

Phe Phe Thr Asn Gln Ala Tyr Ala Ile Ala Ser Ser Ile Val Ser Phe
        195                 200                 205

Tyr Val Pro Leu Val Ile Met Val Phe Val Tyr Ser Arg Val Phe Gln
    210                 215                 220

Glu Ala Lys Arg Gln Leu Gln Lys Ile Asp Lys Ser Glu Gly Arg Phe
225                 230                 235                 240

His Val Gln Asn Leu Ser Gln Val Glu Gln Asp Gly Arg Thr Gly His
                245                 250                 255

Gly Leu Arg Arg Ser Ser Lys Phe Cys Leu Lys Glu His Lys Ala Leu
            260                 265                 270

Lys Thr Leu Gly Ile Ile Met Gly Thr Phe Thr Leu Cys Trp Leu Pro
        275                 280                 285

Phe Phe Ile Val Asn Ile Val His Val Ile Gln Asp Asn Leu Ile Arg
    290                 295                 300

Lys Glu Val Tyr Ile Leu Leu Asn Trp Ile Gly Tyr Val Asn Ser Gly
305                 310                 315                 320

Phe Asn Pro Leu Ile Tyr Cys Arg Ser Pro Asp Phe Arg Ile Ala Phe
                325                 330                 335
```

Gln Glu Leu Leu Cys Leu Arg Arg Ser Ser Leu Lys Ala Tyr Gly Asn
                340                 345                 350

Gly Tyr Ser Ser Asn Gly Asn Thr Gly Glu Gln Ser Gly Tyr His Val
                355                 360                 365

Glu Gln Glu Lys Glu Asn Lys Leu Leu Cys Asp Leu Pro Gly Thr
            370                 375                 380

Glu Asp Phe Val Gly His Gln Gly Thr Val Pro Ser Asp Asn Ile Asp
385                 390                 395                 400

Ser Gln Gly Arg Asn Cys Ser Thr Asn Asp Ser Leu Leu
                405                 410

<210> SEQ ID NO 2
<211> LENGTH: 73
<212> TYPE: PRT
<213> ORGANISM: artificial
<220> FEATURE:
<223> OTHER INFORMATION: synthetic polypeptide

<400> SEQUENCE: 2

Glu Glu Glu Glu Lys Lys Lys Gln Gln Glu Glu Glu Ala Glu Arg Leu
1               5                   10                  15

Arg Arg Ile Gln Glu Glu Met Glu Lys Glu Arg Lys Arg Arg Glu Glu
            20                  25                  30

Asp Glu Glu Arg Arg Arg Lys Glu Glu Glu Arg Arg Met Lys Leu
        35                  40                  45

Glu Met Glu Ala Lys Arg Lys Gln Glu Glu Glu Arg Lys Lys Arg
    50                  55                  60

Glu Asp Asp Glu Lys Arg Lys Lys Lys
65                  70

<210> SEQ ID NO 3
<211> LENGTH: 206
<212> TYPE: PRT
<213> ORGANISM: artificial
<220> FEATURE:
<223> OTHER INFORMATION: synthetic polypeptide

<400> SEQUENCE: 3

Glu Glu Glu Glu Lys Lys Lys Glu Glu Glu Glu Lys Lys Gln Lys Glu
1               5                   10                  15

Glu Gln Glu Arg Leu Ala Lys Glu Glu Ala Arg Lys Gln Lys Glu
            20                  25                  30

Glu Gln Glu Arg Leu Ala Lys Glu Glu Ala Arg Lys Gln Lys Glu
        35                  40                  45

Glu Glu Glu Arg Lys Gln Lys Glu Glu Glu Glu Arg Lys Gln Lys Glu
    50                  55                  60

Glu Glu Glu Arg Lys Leu Lys Glu Glu Gln Glu Arg Lys Ala Ala Glu
65                  70                  75                  80

Glu Lys Lys Ala Lys Glu Glu Ala Glu Arg Lys Ala Lys Glu Glu Gln
                85                  90                  95

Glu Arg Lys Ala Glu Glu Glu Arg Lys Lys Glu Glu Glu Glu Arg
            100                 105                 110

Leu Glu Arg Glu Arg Lys Glu Arg Glu Gln Glu Lys Lys Ala Lys
        115                 120                 125

Glu Glu Ala Glu Arg Ile Ala Lys Leu Glu Ala Glu Lys Lys Ala Glu
    130                 135                 140

Glu Arg Lys Ala Lys Glu Glu Glu Arg Lys Ala Lys Glu Glu
145                 150                 155                 160

Glu Glu Arg Lys Lys Lys Glu Glu Gln Glu Arg Leu Ala Lys Lys
                165                 170                 175

Glu Glu Ala Glu Arg Lys Ala Ala Glu Glu Lys Lys Ala Lys Glu Glu
            180                 185                 190

Gln Glu Arg Lys Glu Lys Glu Glu Ala Glu Arg Lys Gln Arg
        195                 200                 205

<210> SEQ ID NO 4
<211> LENGTH: 39
<212> TYPE: DNA
<213> ORGANISM: artificial
<220> FEATURE:
<223> OTHER INFORMATION: synthetic oligonucleotide

<400> SEQUENCE: 4
atgtatcctt atgatgttcc tgattacgct ggaagtgga                          39

<210> SEQ ID NO 5
<211> LENGTH: 1281
<212> TYPE: DNA
<213> ORGANISM: artificial
<220> FEATURE:
<223> OTHER INFORMATION: synthetic oligonucleotide

<400> SEQUENCE: 5
atggggcaac ccgggaacgg cagcgccttc ttgctggcac ccaatagaag ccatgcgccg      60
gaccacgacg tcacgcagca aagggacgag gtgtgggtgg tgggcatggg catcgtcatg     120
tctctcatcg tcctggccat cgtgtttggc aatgtgctgg tcatcacagc cattgccaag     180
ttcgagcgtc tgcagacggt caccaactac ttcatcactt cactggcctg tgctgatctg     240
gtcatgggcc tggcagtggt gcccctttgg gccgcccata ttcttatgaa aatgtggact     300
tttggcaact tctggtgcga gttttggact tccattgatg tgctgtgcgt cacggccagc     360
attgagaccc tgtgcgtgat cgcagtggat cgctactttg ccattacttc accttttcaag    420 taccagagcc tgctgaccaa gaataaggcc cgggtgatca ttctgatggt gtggattgtg     480
tcaggcctta cctccttctt gcccattcag atgcactggt accgggccac ccaccaggaa     540
gccatcaact gctatgccaa tgagacctgc tgtgacttct tcacgaacca agcctatgcc     600
attgcctctt ccatcgtgtc cttctacgtt ccctggtga tcatggtctt cgtctactcc      660
agggtctttc aggaggccaa aaggcagctc cagaagatta caaatctga gggccgcttc     720 catgtccaga accttagcca ggtggagcag gatgggcgga cggggcatgg actccgcaga     780
tcttccaagt tctgcttgaa ggagcacaaa gccctcaaga cgttaggcat catcatgggc     840
actttcaccc tctgctggct gccccttcttc atcgttaaca ttgtgcatgt gatccaggat     900
aacctcatcc gtaaggaagt ttacatcctc ctaaattgga taggctatgt caattctggt     960
ttcaatcccc ttatctactg ccggagccca gatttcagga ttgccttcca ggagcttctg    1020
tgcctgcgca ggtcttcttt gaaggcctat gggaatggct actccagcaa cggcaacaca    1080
ggggagcaga gtgatatca cgtggaacag gagaaagaaa ataaactgct gtgtgaagac    1140
ctcccaggca cggaagactt tgtgggccat caaggtactg tgcctagcga taacattgat    1200
tcacaaggga ggaattgtag tacaaatgac tcactgctgt ctagaggaag cggaggaagc    1260
ggaggaagcg gaggaagcgg a                                            1281

<210> SEQ ID NO 6
<211> LENGTH: 768
<212> TYPE: DNA
<213> ORGANISM: artificial
<220> FEATURE:
<223> OTHER INFORMATION: synthetic oligonucleotide

<400> SEQUENCE: 6

| | |
|---|---|
| gtgagcaagg gcgaggagct gttcaccggg gtggtgccca tcctggtcga gctggacggc | 60 |
| gacgtaaacg gccacaagtt cagcgtgtcc ggcgagggcg agggcgatgc cacctacggc | 120 |
| aagctgaccc tgaagttcat ctgcaccacc ggcaagctgc ccgtgccctg gcccaccctc | 180 |
| gtgaccacct tcggctacgg cctgatgtgc ttcgcccgct accccgacca catgaagcag | 240 |
| cacgacttct tcaagtccgc catgcccgaa ggctacgtcc aggagcgcac catcttcttc | 300 |
| aaggacgacg gcaactacaa gacccgcgcc gaggtgaagt tcgagggcga caccctggtg | 360 |
| aaccgcatcg agctgaaggg catcgacttc aaggaggacg gcaacatcct ggggcacaag | 420 |
| ctggagtaca actacaacag ccacaacgtc tatatcatgg ccgacaagca gaagaacggc | 480 |
| atcaaggtga acttcaagat ccgccacaac atcgaggacg gcagcgtgca gctcgccgac | 540 |
| cactaccagc agaacacccc catcggcgac ggccccgtgc tgctgcccga caaccactac | 600 |
| ctgagctacc agtccaaact gagcaaagac cccaacgaga gcgcgatca catggtcctg | 660 |
| ctggagttcg tgaccgccgc cgggatcact ctcggcatgg acgagctgta caaggaattc | 720 |
| ggaagcggag gaagcggaga aaacctgtat tttcagggcg aagcgga | 768 |

<210> SEQ ID NO 7
<211> LENGTH: 237
<212> TYPE: DNA
<213> ORGANISM: artificial
<220> FEATURE:
<223> OTHER INFORMATION: synthetic oligonucleotide

<400> SEQUENCE: 7

| | |
|---|---|
| gaagaggaag agaaaaaaaa acagcaggaa gaggaagcag aaaggctgag gcgtattcaa | 60 |
| gaagaaatgg aaaaggaaag aaaaagacgt gaagatgacg aacaacgtcg aagaaaggaa | 120 |
| gaggaggaaa ggcggatgaa acttgagatg gaagcaaaga gaaaacaaga agaagaagag | 180 |
| agaaagaaaa gggaagatga tgaaaaacgc aagaagaagg gctctggcgg ctctggc | 237 |

<210> SEQ ID NO 8
<211> LENGTH: 750
<212> TYPE: DNA
<213> ORGANISM: artificial
<220> FEATURE:
<223> OTHER INFORMATION: synthetic oligonucleotide

<400> SEQUENCE: 8

| | |
|---|---|
| gtgagcaagg gcgaggagct gttcaccggg gtggtgccca tcctggtcga gctggacggc | 60 |
| gacgtaaacg gccacaagtt cagcgtgtcc ggcgagggcg agggcgatgc cacctacggc | 120 |
| aagctgaccc tgaagttcat ctgcaccacc ggcaagctgc ccgtgccctg gcccaccctc | 180 |
| gtgaccaccc tgacctgggg cgtgcagtgc ttcgcccgct accccgacca catgaagcag | 240 |
| cacgacttct tcaagtccgc catgcccgaa ggctacgtcc aggagcgcac catcttcttc | 300 |
| aaggacgacg gcaactacaa gacccgcgcc gaggtgaagt tcgagggcga caccctggtg | 360 |
| aaccgcatcg agctgaaggg catcgacttc aaggaggacg gcaacatcct ggggcacaag | 420 |
| ctggagtaca acgccatcag cgacaacgtc tatatcaccg ccgacaagca gaagaacggc | 480 |

```
atcaaggcca acttcaagat ccgccacaac atcgaggacg gcagcgtgca gctcgccgac      540
cactaccagc agaacacccc catcggcgac ggccccgtgc tgctgcccga caaccactac      600
ctgagcaccc agtccaagct gagcaaagac cccaacgaga agcgcgatca catggtcctg      660
ctggagttcg tgaccgccgc cgggatcact ctcggcatgg acgagctgta caagttaatt      720
aacggaagcg gcgggtcagg tggaagtgga                                       750

<210> SEQ ID NO 9
<211> LENGTH: 81
<212> TYPE: DNA
<213> ORGANISM: artificial
<220> FEATURE:
<223> OTHER INFORMATION: synthetic oligonucleotide

<400> SEQUENCE: 9
gacactgaga acatccgccg tgtgttcaac gactgccgtg acatcattca gcgcatgcac       60
cttcgtcagt acgagctgct c                                                 81

<210> SEQ ID NO 10
<211> LENGTH: 17
<212> TYPE: PRT
<213> ORGANISM: Homo sapiens

<400> SEQUENCE: 10

Met Arg Pro Gln Ile Leu Leu Leu Leu Ala Leu Leu Thr Leu Gly Leu
1               5                   10                  15

Ala
```

G PROTEIN-COUPLED RECEPTOR (GPCR) LIGAND ASSAY

CROSS-REFERENCE TO RELATED APPLICATIONS

This application is a National Stage application under 35 U.S.C. § 371 of International Application No. PCT/US2018/063827 having an International Filing Date of Dec. 4, 2018, which claims benefit of priority from U.S. Provisional Application No. 62/646,534, filed Mar. 22, 2018, and U.S. Provisional Application No. 62/594,356, filed Dec. 4, 2017, all of which are incorporated herein by reference in their entirety.

STATEMENT AS TO FEDERALLY SPONSORED RESEARCH

This invention was made with government support under GM105646, CA186752, and GM126940 awarded by the National Institutes of Health. The government has certain rights in the invention.

TECHNICAL FIELD

This document relates to materials and methods for assessing the effects of various ligands on their receptors, including, for example, materials and methods for assessing the intrinsic effects of various ligands on G protein-coupled receptors (GPCRs).

BACKGROUND

GPCRs are the target of over one-third of all pharmaceuticals in modern drug therapies. Small-molecule therapeutics that bind GPCRs can influence cellular processes by either enhancing downstream signaling (agonist) or blocking the effects of endogenous ligands (antagonist/inverse agonist) (Tyndall and Sandilya (2005) *Med. Chem.* 1, 405-421). The precise effects of GPCR therapeutics on cell signaling are tissue and cell-type dependent, however, thereby limiting the ability to translate information derived from cell-based assays to the on-target effects in physiological and pathophysiological contexts.

To date, the stimulating effect of a ligand at the level of a single GPCR, referred to as "intrinsic efficacy," has best been approximated by measuring the activation rate of G proteins that couple to the GPCR (Harrison and Traynor (2003) *Life Sci.* 74, 489-508; Denis et al. (2012) *Curr. Pharm. Des.* 18, 128-144; and Gregorio et al. (2017) *Nature* 10.1038/nature22354). G protein activation assays that utilize either live cells or crude membrane preparations containing the GPCR are complicated by the heterogeneity inherent in different cell or membrane batches. An alternative approach (Gregorio et al., supra) uses extensive single molecule measurements with GPCRs and G proteins purified to homogeneity to define a "molecular efficacy" that currently is the closest approximation in the field to the intrinsic efficacy, but this approach requires procedure-optimization for each GPCR and is resource-intensive for examining large numbers of compounds. Other studies have used a Forster resonance energy transfer- (FRET-) based biosensor based on Systematic Protein Affinity Strength Modulation (SPASM) technology to detect ligand-induced interaction between a GPCR and the C-terminus of the Gα subunit of a G protein in live cells (Malik et al. (2013) *J Biol. Chem.* 288, 17167-17178), and to examine the selectivity of G protein activation by GPCRs (Semack et al. (2016) *J. Biol. Chem.* 291, 17929-17940).

SUMMARY

This document is based, at least in part, on the development of a system and an assay that can effectively compare the intrinsic effects of ligands on GPCRs. The systems and methods described herein include the use of Giant Plasma Membrane Vesicles (GPMVs) derived from cells expressing SPASM sensors (e.g., SPASM GPCR sensors). Purified GPMVs incorporate the SPASM sensors within their lipid bilayer, while maintaining protein function. As discussed herein, the GPMV-incorporated SPASM sensors ("GPMV sensors") are highly stable, making them a scalable reagent suitable for high-throughput drug screening and analysis. Since they are incorporated into the GPMV membrane, the SPASM GPCR sensors are in their native environment and can maintain their native conformation. FRET measurements using SPASM GPCR sensors in live cells can be sensitive to expression levels, cell handling, and ligand stimulation times. Unlike live cells, GPMV sensors provide consistency and reliability in FRET measurements, regardless of expression levels, handling, and ligand stimulation time. Using this novel reagent, the relationship between ligand-induced changes in FRET intensity and intrinsic efficacy has been investigated for GPCRs, demonstrating that FRET measurements correlate directly with reported intrinsic efficacy ($R^2$=0.99) and activation rate of G proteins that couple to a GPCR ($R^2$=0.97) (Gregorio et al., supra). The data described in the Examples herein support the combined application of GPMVs and SPASM GPCR sensors as a novel FRET-based assay for precisely measuring the intrinsic efficacy of GPCR ligands.

In a first aspect, this document provides a giant plasma membrane vesicle (GPMV) sensor containing a membrane-associated polypeptide, where the membrane-associated polypeptide contains a target G protein-coupled receptor (GPCR), a linker including an amino acid sequence flanked by a FRET donor and a FRET acceptor, and a receptor partner for the target GPCR, where the linker separates the target GPCR from the receptor partner. The linker can be about 10 nm to about 30 nm in length. The linker can include an ER/K sequence having a substantially repeating sequence of glutamic acid, arginine, and lysine residues, and can be about 50 to about 250 amino acids in length. In some cases, the linker can include the amino acid sequence set forth in SEQ ID NO:2, or a sequence that is at least 95% identical to the sequence set forth in SEQ ID NO:2. The receptor partner can be a peptide, polypeptide, protein, or protein domain. The membrane-associated polypeptide can further contain a (Gly-Ser-Gly)$_2$-4 amino acid sequence on either side of the FRET donor and the FRET acceptor. The FRET donor can be monomeric Cerulean or monomeric enhanced green fluorescent protein (eGFP), and the FRET acceptor can be monomeric Citrine or monomeric Cherry. In some cases, the membrane-associated polypeptide can include, in order from amino terminus to carboxy terminus, the target GPCR, a first (Gly-Ser-Gly)$_{2-4}$ amino acid sequence, a FRET donor or acceptor, a second (Gly-Ser-Gly)$_{2-4}$ amino acid sequence, the linker, a third (Gly-Ser-Gly)$_{2-4}$ amino acid sequence, a partner for the FRET donor or acceptor, a fourth (Gly-Ser-Gly)$_{2-4}$ amino acid sequence, and the receptor partner for the target GPCR.

In another aspect, this document features a method for quantifying the intrinsic efficacy of a compound for a target GPCR. The method can include (a) providing a GPMV sensor, where the sensor contains a GPMV that includes a membrane-associated polypeptide, the membrane-associated polypeptide containing a target GPCR, a linker including an amino acid sequence flanked by a FRET donor and a FRET acceptor, and a receptor partner for the target GPCR, where the linker separates the target GPCR from the receptor partner; (b) measuring an initial FRET ratio for the sensor; (c) contacting the sensor with a compound that interacts with the target GPCR; (d) measuring a test FRET ratio for the sensor; and (e) calculating the intrinsic efficacy of the compound based on the difference between the test FRET ratio and the initial FRET ratio. The linker can be about 10 nm to about 30 nm in length. The linker can contain an ER/K sequence having a substantially repeating sequence of glutamic acid, arginine, and lysine residues, and can be about 50 to about 250 amino acids in length. In some cases, the linker can contain the amino acid sequence set forth in SEQ ID NO:2, or a sequence that is at least 95% identical to the sequence set forth in SEQ ID NO:2. The receptor partner can be a peptide, polypeptide, protein, or protein domain. The membrane-associated polypeptide can further contain a (Gly-Ser-Gly)$_{2-4}$ amino acid sequence on either side of the FRET donor and the FRET acceptor. The FRET donor can be monomeric Cerulean or monomeric eGFP, and the FRET acceptor can be monomeric Citrine or monomeric Cherry. In some cases, the membrane-associated polypeptide can contain, in order from amino terminus to carboxy terminus, the target GPCR, a first (Gly-Ser-Gly)$_{2-4}$ amino acid sequence, a FRET donor or acceptor, a second (Gly-Ser-Gly)$_{2-4}$ amino acid sequence, the linker, a third (Gly-Ser-Gly)$_{2-4}$ amino acid sequence, a partner for the FRET donor or acceptor, a fourth (Gly-Ser-Gly)$_{2-4}$ amino acid sequence, and the receptor partner for the target GPCR.

In another aspect, this document features a method for identifying a compound that interacts with a target GPCR. The method can include (a) providing a GPMV sensor, where the sensor contains a GPMV that includes a membrane-associated polypeptide, the membrane-associated polypeptide containing a target GPCR, a linker including an amino acid sequence flanked by a FRET donor and a FRET acceptor, and a receptor partner for the target GPCR, where the linker separates the target GPCR from the receptor partner; (b) measuring an initial FRET ratio for the sensor; (c) contacting the sensor with a candidate compound; (d) measuring a test FRET ratio for the sensor; and (e) identifying the candidate compound as interacting with the target GPCR when the test FRET ratio is altered by at least 0.5% as compared to the initial FRET ratio. The linker can be about 10 nm to about 30 nm in length. The linker can include an ER/K sequence having a substantially repeating sequence of glutamic acid, arginine, and lysine residues, and can be about 50 to about 250 amino acids in length. In some cases, the linker can include the amino acid sequence set forth in SEQ ID NO:2, or a sequence that is at least 95% identical to the sequence set forth in SEQ ID NO:2. The receptor partner can be a peptide, polypeptide, protein, or protein domain. The membrane-associated polypeptide can further contain a (Gly-Ser-Gly)$_{2-4}$ amino acid sequence on either side of the FRET donor and the FRET acceptor. The FRET donor can be monomeric Cerulean or monomeric eGFP, and the FRET acceptor can be monomeric Citrine or monomeric Cherry. In some cases, the membrane-associated polypeptide can contain, in order from amino terminus to carboxy terminus, the target GPCR, a first (Gly-Ser-Gly)$_{2-4}$ amino acid sequence, a FRET donor or acceptor, a second (Gly-Ser-Gly)$_{2-4}$ amino acid sequence, the linker, a third (Gly-Ser-Gly)$_{2-4}$ amino acid sequence, a partner for the FRET donor or acceptor, a fourth (Gly-Ser-Gly)$_{2-4}$ amino acid sequence, and the receptor partner for the target GPCR. The method can further include providing two or more GPMV sensors, each containing a different target GPCR, measuring initial and test FRET ratios for each GPMV sensor, and identifying the candidate compound as a GPCR-specific ligand when at least some of the test FRET ratios are not altered by at least 0.5% as compared to the initial FRET ratios.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1A is a schematic of the GPCR-SPASM sensors used in the studies described herein (top), and a diagram of the sensors in dissociated (low FRET) and associated (high FRET) states (bottom).

FIGS. 7A-7C are a series of graphs showing that GPMV-β2AR-Spep ΔFRET does not correlate with factors that dictate classical efficacy. GPMV-β2AR-Spep sensors were stimulated with various ligands and the ΔFRET were plotted against previously documented measurements of experimental factors that dictate ligand efficacy ratio (Baker, supra). Error bars denote s.e.m. Data are derived from at least three independent experiments, with at least three replicates per condition. $R^2=0.61$ for cAMP vs ΔFRET (FIG. 7A), 0.32 for $-\log[EC_{50}]$ vs ΔFRET (FIG. 7B), and 0.09 for $-\log K_d$ vs ΔFRET (FIG. 7C). In addition, $R^2=0.25$ for $EC_{50}$ vs ΔFRET and 0.04 for $K_d$ vs ΔFRET (not shown).

DETAILED DESCRIPTION

Figure 1B:
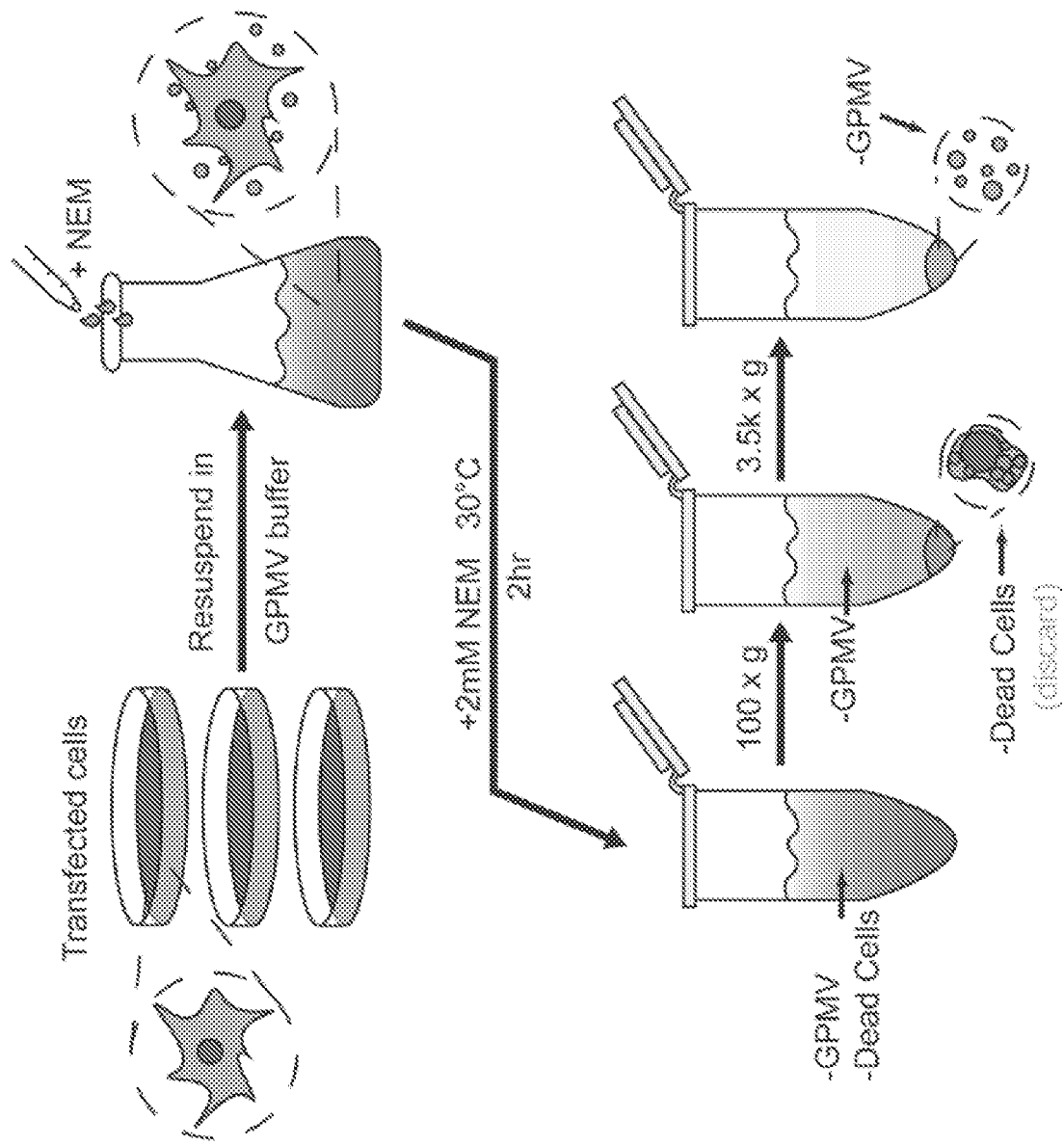
FIG. 1B is a schematic diagram depicting a process for synthesizing and purifying GPMVs.

The materials and methods provided herein can effectively be used to identify ligands for protein targets, and to compare the intrinsic effects of ligands on GPCRs. In particular, as described herein, GPMVs derived from cells expressing SPASM sensors incorporate the SPASM sensors within their lipid bilayer, and the SPASM molecules remain functional since the receptor portion of the SPASM molecule can be present in its native environment within the membrane. The GPMV sensors are a highly stable, consistent, reliable, and scalable reagent suitable for high-throughput drug screening and analysis.

Thus, the materials and methods described herein provide means for identifying and assessing interactions between molecules, such as ligands and receptors, or other proteins having a function that can be modulated by interaction with an activator or inhibitor, for example. Thus, this document provides, inter alia, sensors that include a GPMV and a chimeric polypeptide that can be used as a tool to determine whether a candidate compound (e.g., a peptide, nucleic acid, small molecule, or biologic) interacts with a particular target, and to assess the intrinsic effects of the candidate compound on the target.

Treating live cells with the organic compound N-ethylmaleimide (NEM) induces vesiculation of the cell membrane, yielding large ("giant") vesicles that are composed of cytoplasm and plasma membrane. These GPMVs incorporate membrane-associated proteins from the originating cell, but lack any intracellular organelles. GPMVs have been used as a tool to, for example, investigate phase separation in eukaryotic membranes (Sezgin et al. (2012) Nat. Protoc. 7, 1042-1051), and for the study of membrane proteins such as the immunoglobulin E receptor (IgE-R) and fibroblast growth factor receptor (FGFR3) (Sarabipour and Hristova (2016) Biochim. Biophys. Acta—Biomembr. 1858, 1436-1442; and Holowka and Baird (1983) Biochemistry 22, 3466-3474). The lack of intracellular membranous structures in GPMVs provides an adaptable platform for segregating membrane integrated receptors such as GPCRs from the regulation machinery of the cytoplasm.

SPASM is a protein engineering technique for modulating and analyzing the interaction between two proteins and/or peptides (Malik et al., supra; and Sivaramakrishnan and Spudich (2011) Proc. Natl. Acad. Sci. USA 108, 20467-20472. A SPASM sensor is a single polypeptide composed of two proteins of interest fused together at either end of an ER/K α-helix linker (e.g., as depicted in FIG. 1A). The presence of a FRET donor and a FRET acceptor that can be present on either side of the linker (between the linker and the proteins of interest), or at the N- and C-termini of the sensor, allows for quantification of protein-protein interaction in live cells. The length of the ER/K linker dictates the relative concentration of the N and C terminal proteins by regulating the on-rate of the proteins, without affecting the off-rate (Sivaramakrishnan and Spudich, supra). Thus, SPASM provides pairwise control over stoichiometry (1:1), co-localization, and relative concentration. SPASM sensors are modular and can be adapted to control and/or monitor interactions between a receptor (e.g., a GPCR) and a peptide or a protein domain derived from a different binding partner, such as a G protein subunit for a SPASM GPCR sensor.

As described herein, this document provides GPMVs containing SPASM polypeptides, nucleic acids encoding the polypeptides, host cells containing the nucleic acids, and methods for making and using the GPMVs, cells, polypeptides, and nucleic acids.

The term "polypeptide" as used herein refers to a compound of two or more subunit amino acids, regardless of post-translational modification (e.g., phosphorylation or glycosylation). The subunits may be linked by peptide bonds or other bonds such as, for example, ester or ether bonds. The term "amino acid" refers to either natural and/or unnatural or synthetic amino acids, including D/L optical isomers.

By "isolated" or "purified" with respect to a polypeptide it is meant that the polypeptide is separated to some extent from cellular components with which it normally is found in nature (e.g., other polypeptides, lipids, carbohydrates, and nucleic acids). A purified polypeptide can yield a single major band on a non-reducing polyacrylamide gel. A purified polypeptide can be at least about 75% pure (e.g., at least 80%, 85%, 90%, 95%, 97%, 98%, 99%, or 100% pure). Purified polypeptides can be obtained by, for example, extraction from a natural source, by chemical synthesis, or by recombinant production in a host cell or transgenic plant, and can be purified using, for example, affinity chromatography, immunoprecipitation, size exclusion chromatography, and ion exchange chromatography. The extent of purification can be measured using any appropriate method, including, without limitation, column chromatography, polyacrylamide gel electrophoresis, or high-performance liquid chromatography.

The terms "nucleic acid" and "polynucleotide" can be used interchangeably, and refer to both RNA and DNA, including cDNA, genomic DNA, synthetic (e.g., chemically synthesized) DNA, and DNA (or RNA) containing nucleic acid analogs. Polynucleotides can have any three-dimensional structure. A nucleic acid can be double-stranded or single-stranded (i.e., a sense strand or an antisense single strand). Non-limiting examples of polynucleotides include genes, gene fragments, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers, as well as nucleic acid analogs.

The percent sequence identity between a particular nucleic acid or amino acid sequence and a sequence referenced by a particular sequence identification number is determined as follows. First, a nucleic acid or amino acid sequence is compared to the sequence set forth in a particular sequence identification number using the BLAST 2 Sequences (Bl2seq) program from the stand-alone version of BLASTZ containing BLASTN version 2.0.14 and BLASTP version 2.0.14. This stand-alone version of BLASTZ can be obtained online at fr.com/blast or at ncbi.nlm.nih.gov. Instructions explaining how to use the Bl2seq program can be found in the readme file accompanying BLASTZ. Bl2seq performs a comparison between two sequences using either the BLASTN or BLASTP algorithm. BLASTN is used to compare nucleic acid sequences, while BLASTP is used to compare amino acid sequences. To compare two nucleic acid sequences, the options are set as follows: -i is set to a file containing the first nucleic acid sequence to be compared (e.g., C:\seq1.txt); -j is set to a file containing the second nucleic acid sequence to be compared (e.g., C:\seq2.txt); -p is set to blastn; -o is set to any desired file name (e.g., C:\output.txt); -q is set to −1; -r is set to 2; and all other options are left at their default setting. For example, the following command can be used to generate an output file containing a comparison between two sequences: C:\Bl2seq c:\seq1.txt -j c:\seq2.txt -p blastn -o c:\output.txt -q −1 -r 2. To compare two amino acid sequences, the options of Bl2seq are set as follows: -i is set to a file containing the first amino acid sequence to be compared (e.g., C:\seq1.txt); -j is set to a file containing the second amino acid sequence to be compared (e.g., C: \seq2.txt); -p is set to blastp; -o is set to any desired file name (e.g., C:\output.txt); and all other options are left at their default setting. For example, the following command can be used to generate an output file containing a comparison between two amino acid sequences: C:\Bl2seq c:\seq1.txt -j c:\seq2.txt -p blastp -o c:\output.txt. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence (e.g., SEQ ID NO:1), or by an articulated length (e.g., 100 consecutive nucleotides or amino acid residues from a sequence set forth in an identified sequence), followed by multiplying the resulting value by 100. For example, an amino acid sequence that has 400 matches when aligned with the sequence set forth in SEQ ID NO:1 is 96.7 percent identical to the sequence set forth in SEQ ID NO:1 (i.e., 400±413×100=96.7). It is noted that the percent sequence identity value is rounded to the nearest tenth. For example, 75.11, 75.12, 75.13, and 75.14 is rounded down to 75.1, while 75.15, 75.16, 75.17, 75.18, and 75.19 is rounded up to 75.2. It also is noted that the length value will always be an integer.

The nucleic acids may be incorporated into or contained within recombinant nucleic acid constructs such as vectors. A "vector" is a replicon, such as a plasmid, phage, or cosmid, into which another DNA segment may be inserted so as to bring about the replication of the inserted segment. Generally, a vector is capable of replication when associated with the proper control elements. Suitable vector backbones include, for example, those routinely used in the art such as plasmids, viruses, artificial chromosomes, BACs, YACs, or PACs. The term "vector" includes cloning and expression vectors, as well as viral vectors and integrating vectors. An "expression vector" is a vector that includes one or more "expression control sequences" that control or regulate the transcription and/or translation of another DNA sequence. Suitable expression vectors include, without limitation, plasmids and viral vectors derived from, for example, bacteriophage, baculoviruses, tobacco mosaic virus, herpes viruses, cytomegalovirus, retroviruses, vaccinia viruses, adenoviruses, and adeno-associated viruses. Numerous vectors and expression systems are commercially available from such corporations as Novagen (Madison, WI), Clontech (Palo Alto, CA), Stratagene (La Jolla, CA), and Invitrogen/Life Technologies (Carlsbad, CA).

Host cells containing a nucleic acid or vector also are provided herein. Suitable host cells can include, without limitation, bacterial cells, yeast cells, and human or non-human mammalian cells (e.g., HEK 293 cells, 3T3 cells, or HeLa cells). Methods for making GPMVs containing GPCR sensor polypeptides from such host cells also are provided herein. Suitable methods for preparing GPMVs include, without limitation, those described in the Examples below.

In some embodiments, this document provides GPMVs containing chimeric sensor polypeptides that contain (a) a target GPCR; (b) a linker containing an amino acid sequence flanked by a FRET donor and a FRET acceptor; and (c) a receptor partner for the target GPCR. As used herein, the "receptor partner" can be a peptide, polypeptide, protein, or protein domain having affinity for the target GPCR. Interactions between the target GPCR and the receptor partner can be detected based on fluorescence that results when the FRET donor and FRET acceptor interact. Interaction between a test compound and the target GPCR can be detected based on a change in the FRET ratio for the sensor before and after addition of the test compound to the GPMV sensor.

The target GPCR may be any member of the GPCR superfamily. Amino acid sequences for GPCRs include those known in the art and available in, for example, GENBANK®. In some cases, a chimeric polypeptide can include an amino acid sequence that is at least 90% (e.g., at least 91%, at least 92%, at least 93%, at least 94%, at least 95%, at least 96%, at least 97%, at least 98%, or at least 99%) identical to a known amino acid sequence for a GPCR. Non-limiting examples of GPCRs include, without limitation, β2AR, vasopressin1 receptor (V1R), and α1AR. A non-limiting example of a representative amino acid sequence for a GPCR is set forth in SEQ ID NO:1, which is the sequence of the human beta 2 adrenergic receptor:

(SEQ ID NO: 1)
MGQPGNGSAFLLAPNRSHAPDHDVTQQRDEVWVVGMGIVMSLIVLAIVF

GNVLVITAIAKFERLQTVTNYFITSLACADLVMGLAVVPFGAAHILMKM

WTFGNFWCEFWTSIDVLCVTASIETLCVIAVDRYFAITSPFKYQSLLTK

NKARVIILMVWIVSGLTSFLPIQMHWYRATHQEAINCYANETCCDFFTN

QAYAIASSIVSFYVPLVIMVFVYSRVFQEAKRQLQKIDKSEGRFHVQNL

SQVEQDGRTGHGLRRSSKFCLKEHKALKTLGIIMGTFTLCWLPFFIVNI

VHVIQDNLIRKEVYILLNWIGYVNSGFNPLIYCRSPDFRIAFQELLCLR

RSSLKAYGNGYSSNGNTGEQSGYHVEQEKENKLLCEDLPGTEDFVGHQG

TVPSDNIDSQGRNCSTNDSLL.

The linker can be positioned between the target GPCR and the receptor partner. Such positioning can permit the target GPCR and the receptor partner to move relative to one another. The linker can have a length of about 8 nm to about 35 nm (e.g., about 8 to 10 nm, about 10 to 15 nm, about 15 to 20 nm, about 20 to 25 nm, about 25 to 30 nm, about 30 to 35 nm, or about 10 to 30 nm). In some embodiments, the polypeptide linker can include an "ER/K" sequence that includes a substantially repeating sequence of glutamic acid, arginine, and lysine residues. For example, the linker may include the sequence set forth in SEQ ID NO:2 (EEEEKKKQQEEEAE RLRRIQEEMEKERKR-REEDEERRRKEEEERRMKLE-MEAKRKQEEEERKKRED DEKRKKK), or a sequence that is at least 90% (e.g., at least 91%, at least 92%, at least 93%, at least 94%, at least 95%, at least 96%, at least 97%, at least 98%, or at least 99%) identical to SEQ ID NO:2, or the linker may include the sequence set forth in SEQ ID NO:3 (EEEEKKKEEEEKKQKEEQERLAKEEAERKQ-KEEQERLAKE EAERKQKEEEERKQKEEEERKQ-KEEEERKLKEEQERKAAEEKKAKEEAERK AKE-EQERKAEEERKKKEEEERLERERKEREEQEKKAKE-EAERIAKLEAEKKA EEERKAKEEEERKA-KEEEERKKKEEQERLAKEKEEAERKAAEEKKAKE-EQER KEKEEAERKQR), or a sequence that is at least 90% (e.g., at least 91%, at least 92%, at least 93%, at least 94%, at least 95%, at least 96%, at least 97%, at least 98%, or at least 99%) identical to SEQ ID NO:3. Typically, the linker will be about 50 to about 250 (e.g., about 50 to about 75, about 75 to about 100, about 50 to about 100, about 100 to about 150, about 150 to about 200, about 100 to about 200, or about 200 to about 250) amino acids in length.

It is to be noted that the GPCR sensors in the GPMVs provided herein can include any suitable resonance energy transfer donor and acceptor pairs. As described in the Examples herein, for example, mCitrine and mCerulean can be used, but other useful fluorophores include cyan fluorescent proteins (e.g., AmCyan1), green fluorescent proteins (e.g., eGFP, AcGFP1, and ZsGreen1), yellow fluorescent proteins (e.g., ZsYellow1 and mBanana), orange fluorescent proteins (e.g., mOrange and mOrange2), red fluorescent proteins (e.g., DsRed-Express2, DsRed-Express, tdTomato, DsRed-Monomer, DsRed2, AsRed2, and mStrawberry), far-red fluorescent proteins (e.g., HcRed1, mRaspberry, E2-Crimson, and mPlum), and switchable fluorescent proteins (e.g., Dendra2, Timer, and PAmCherry). All of the aforementioned are available from, for example, Takara Bio USA, Inc. (formerly Clontech Laboratories, Inc.; Mountain View, CA). Other types of resonance energy transfer donors and acceptors can be used, including bioluminescence resonance energy transfer (BRET) donors and/or receptors.

In addition, one or more (e.g., two, three, four, or more than four) Gly-Ser-Gly sequences can be present on either side of the FRET acceptor and the FRET donor, and/or between the FRET donor and acceptor and the ER/K sequence. The inclusion of one or more Gly-Ser-Gly sequences can provide rotational freedom between the target GPCR and the receptor partner, which may facilitate interaction between those regions of the chimeric polypeptide.

Thus, in some cases, the chimeric polypeptides provided herein can include a target GPCR, a linker amino acid sequence that contains a sequence flanked by a FRET donor and a FRET acceptor, and a receptor partner, in addition to one or more optional components (e.g., one or more Gly-Ser-Gly sequences). For example, in some embodiments a chimeric polypeptide contained in a GPMV sensor may contain, in order from amino terminus to carboxy terminus, a target GPCR having affinity for a receptor partner, a $(Gly-Ser-Gly)_{2-4}$ amino acid sequence, a resonance energy transfer donor or acceptor, a $(Gly-Ser-Gly)_{2-4}$ amino acid sequence, a linker containing an amino acid sequence at least 90% identical to the sequence set forth in SEQ ID NO:2 or SEQ ID NO:3, a $(Gly-Ser-Gly)_{2-4}$ amino acid sequence, a partner for the resonance energy transfer donor or acceptor, a $(Gly-Ser-Gly)_{2-4}$ amino acid sequence, and the receptor partner, which has affinity for the target GPCR.

This document also provides nucleic acids that encode the chimeric polypeptides described herein, as well as host cells containing the nucleic acids, and methods for generating GPMV sensors by expressing a chimeric polypeptide in a host cell and then generating GPMVs. Useful methods for transfecting or transforming cells with an expression vector include those known in the art, as well as the methods described in the Examples herein. The methods described in the Examples can be particularly useful, as they include optimized steps.

Also provided herein are methods that can be used to identify compounds (e.g., small molecule compounds or biologics, including peptides and nucleic acids) that interact with target GPCRs. In some embodiments, for example, this document provides methods for identifying a compound that can interact with a receptor. The methods can include providing a GPMV sensor as disclosed herein, for example, where the GPMV sensor includes a chimeric polypeptide that contains (1) a target GPCR that contains at least the ligand binding domain from a selected receptor; (2) a linker that includes an amino acid sequence flanked by a FRET donor and a FRET acceptor; and (3) a receptor partner that binds to the target GPCR, such that the linker separates the target GPCR from the receptor partner. The methods also can include measuring an initial FRET ratio for the sensor, contacting the sensor with a candidate compound (e.g., a small molecule or a biologic), measuring a second FRET ratio for the sensor, and identifying the candidate compound as having affinity for the target if the second FRET ratio is increased by at least 0.5% (e.g., at least 0.5%, 1%, 2%, 3%, 4%, 5%, or more than 5%) as compared to the initial FRET ratio.

In some cases, this method can be used to identify a ligand specific for a particular target GPCR (i.e., a ligand that can detectably bind to a selected GPCR, but that does not bind detectably to other GPCRs). For example, the above-described method can be conducted using a plurality (e.g., two, three, four, five, or more than five) GPMV sensors, where each sensor contains a different target GPCR. In such methods, an initial FRET ratio and a second FRET ratio can be determined for each sensor in the presence of a candidate compound. If a particular sensor exhibits a FRET ratio that is increased by at least 0.5% after addition of the candidate compound (as determined by comparing the second FRET ratio to the initial FRET ratio), but other sensors do not exhibit FRET ratios that are decreased by at least 0.5%, the candidate compound can be identified as a being specific for the target GPCR of the sensor that demonstrated the decreased FRET ratio.

In addition, the methods provided herein can be used to evaluate the intrinsic efficacy of a compound that interacts with a target GPCR. In some cases, such methods can include the following steps:

(a) providing a GPMV sensor containing (i) a target GPCR that contains at least the ligand binding domain from a selected receptor, (ii) a linker that includes an amino acid sequence flanked by a FRET donor and a FRET acceptor, and (iii) a receptor partner that binds to the target GPCR, such that the linker separates the target GPCR from the receptor partner;

(b) measuring an initial FRET ratio for the sensor;

(c) contacting the GPMV sensor with a compound that interacts with the target GPCR;

(d) measuring a second FRET ratio for the GPMV sensor; and (e) determining the intrinsic efficacy of the compound for the target based on the difference between the test FRET ratio and the initial FRET ratio. In addition to or instead of FRET, the readout can include BRET between a luciferase and a fluorophore flanking the linker, and/or changes in fluorescence, bioluminescence, or enzymatic activity triggered by interactions between polypeptides flanking the linker.

It is to be noted that in addition to providing a technology for identifying ligands and evaluating ligand intrinsic efficacy as described herein, the GPMV technology can be more broadly used to maintain GPCR molecules in their native membrane state. This can, in turn, be used to identify GPCR-targeting therapeutics. For example, an anti-GPCR-based drug discovery method may include immunizing a mammal with a GPMV that does not include a GPCR, and then immunizing the mammal with a GPMV that includes a GPCR, in order to raise antibodies against the GPCR. The antibodies can then be used for drug discovery. Such methods would obviate the need to purify individual GPCR proteins in order to use them for raising antibodies, since the GPMV-associated GPCR molecules would be present in their native environment (the lipid bilayer) and, most likely, their native conformation.

The invention will be further described in the following examples, which do not limit the scope of the invention described in the claims.

EXAMPLES

Example 1—Materials and Methods

Sensor construct: The plasmid used in the studies described herein included the following sequences in the pcDNA®5 vector (ThermoFisher Scientific; Waltham, MA).

```
N-terminal HA tag and GSG linker:
                                                    (SEQ ID NO: 4)
ATGTATCCTTATGATGTTCCTGATTACGCTGGAAGTGGA;

β2AR (can be substituted into any other GPCR) and GSG linkers:
                                                    (SEQ ID NO: 5)
ATGGGGCAACCCGGGAACGGCAGCGCCTTCTTGCTGGCACCCAATAGAAGCCAT

GCGCCGGACCACGACGTCACGCAGCAAAGGGACGAGGTGTGGGTGGTGGGC

ATGGGCATCGTCATGTCTCTCATCGTCCTGGCCATCGTGTTTGGCAATGTG

CTGGTCATCACAGCCATTGCCAAGTTCGAGCGTCTGCAGACGGTCACCAA

CTACTTCATCACTTCACTGGCCTGTGCTGATCGGTCATGGGCCTGGCAGT

GGTGCCCTTTGGGGCCGCCCATATTCTTATGAAAATGTGGACTTTTGGCAA

CTTCTGGTGCGAGTTTTGGACTTCCATTGATGTGCTGTGCGTCACGGCCAG

CATTGAGACCCTGTGCGTGATCGCAGTGGATCGCTACTTTGCCATTACTTC
```

-continued

ACCTTTCAAGTACCAGAGCCTGCTGACCAAGAATAAGGCCCGGGTGATCA

TTCTGATGGTGTGGATTGTGTCAGGCCTTACCTCCTTCTTGCCCATTCAGA

TGCACTGGTACCGGGCCACCCACCAGGAAGCCATCAACTGCTATGCCAAT

GAGACCTGCTGTGACTTCTTCACGAACCAAGCCTATGCCATTGCCTCTTCC

ATCGTGTCCTTCTACGTTCCCCTGGTGATCATGGTCTTCGTCTACTCCAGG

GTCTTTCAGGAGGCCAAAAGGCAGCTCCAGAAGATTGACAAATCTGAGGG

CCGCTTCCATGTCCAGAACCTTAGCCAGGTGGAGCAGGATGGGCGGACGG

GGCATGGACTCCGCAGATCTTCCAAGTTCTGCTTGAAGGAGCACAAAGCC

CTCAAGACGTTAGGCATCATCATGGGCACTTTCACCCTCTGCTGGCTGCCC

TTCTTCATCGTTAACATTGTGCATGTGATCCAGGATAACCTCATCCGTAAG

GAAGTTTACATCCTCCTAAATTGGATAGGCTATGTCAATTCTGGTTTCAAT

CCCCTTATCTACTGCCGGAGCCCAGATTTCAGGATTGCCTTCCAGGAGCTT

CTGTGCCTGCGCAGGTCTTCTTTGAAGGCCTATGGGAATGGCTACTCCAGC

AACGGCAACACAGGGGAGCAGAGTGGATATCACGTGGAACAGGAGAAAG

AAAATAAACTGCTGTGTGAAGACCTCCCAGGCACGGAAGACTTTGTGGGC

CATCAAGGTACTGTGCCTAGCGATAACATTGATTCACAAGGGAGGAATTG

TAGTACAAATGACTCACTGCTGTCTAGA<u>GGAAGCGGAGGAAGCGGAGGA</u>

<u>AGCGGAGGAAGCGGA</u>;

mCitrine, *TEV cleavage site*, and <u>GSG linkers</u>:

(SEQ ID NO: 6)

GTGAGCAAGGGCGAGGAGCTGTTCACCGGGGTGGTGCCCATCCTGGTCGAGCTGGAC

GGCGACGTAAACGGCCACAAGTTCAGCGTGTCCGGCGAGGGCGAGGGCGATGCCACCT

ACGGCAAGCTGACCCTGAAGTTCATCTGCACCACCGGCAAGCTGCCCGTG

CCCTGGCCCACCCTCGTGACCACCTTCGGCTACGGCCTGATGTGCTTCGCC

CGCTACCCCGACCACATGAAGCAGCACGACTTCTTCAAGTCCGCCATGCC

CGAAGGCTACGTCCAGGAGCGCACCATCTTCTTCAAGGACGACGGCAACT

ACAAGACCCGCGCCGAGGTGAAGTTCGAGGGCGACACCCTGGTGAACCG

CATCGAGCTGAAGGGCATCGACTTCAAGGAGGACGGCAACATCCTGGGG

CACAAGCTGGAGTACAACTACAACAGCCACAACGTCTATATCATGGCCGA

CAAGCAGAAGAACGGCATCAAGGTGAACTTCAAGATCCGCCACAACATC

GAGGACGGCAGCGTGCAGCTCGCCGACCACTACCAGCAGAACACCCCCAT

CGGCGACGGCCCCGTGCTGCTGCCCGACAACCACTACCTGAGCTACCAGT

CCAAACTGAGCAAAGACCCCAACGAGAAGCGCGATCACATGGTCCTGCTG

GAGTTCGTGACCGCCGCCGGGATCACTCTCGGCATGGACGAGCTGTACAA

GGAATTC<u>GGAAGCGGAGGAAGCGGA</u>*GAAAACCTGTATTTTCAGGGC*<u>GGAAG</u>

<u>CGGA</u>;

10 nm ER/K linker and <u>GSG linkers</u>:

(SEQ ID NO: 7)

GAAGAGGAAGAGAAAAAAAAA

CAGCAGGAAGAGGAAGCAGAAAGGCTGAGGCGTATTCAAGAAGAAATGG

AAAAGGAAAGAAAAAGACGTGAAGATGACGAACAACGTCGAAGAAAGG

AAGAGGAGGAAAGGCGGATGAAACTTGAGATGGAAGCAAAGAGAAAAC

-continued

AAGAAGAAGAAGAGAGAAAGAAAAGGGAAGATGATGAAAAACGCAAGA

AGAAGGGCTCTGGCGGCTCTGGC;

mCerulean and GSG linkers:

(SEQ ID NO: 8)

GTGAGCAAGGGCGAGGAGCTGTTCACCG

GGGTGGTGCCCATCCTGGTCGAGCTGGACGGCGACGTAAACGGCCACAAG

TTCAGCGTGTCCGGCGAGGGCGAGGGCGATGCCACCTACGGCAAGCTGAC

CCTGAAGTTCATCTGCACCACCGGCAAGCTGCCCGTGCCCTGGCCCACCCT

CGTGACCACCCTGACCTGGGGCGTGCAGTGCTTCGCCCGCTACCCCGACC

ACATGAAGCAGCACGACTTCTTCAAGTCCGCCATGCCCGAAGGCTACGTC

CAGGAGCGCACCATCTTCTTCAAGGACGACGGCAACTACAAGACCCGCGC

CGAGGTGAAGTTCGAGGGCGACACCCTGGTGAACCGCATCGAGCTGAAG

GGCATCGACTTCAAGGAGGACGGCAACATCCTGGGGCACAAGCTGGAGT

ACAACGCCATCAGCGACAACGTCTATATCACCGCCGACAAGCAGAAGAA

CGGCATCAAGGCCAACTTCAAGATCCGCCACAACATCGAGGACGGCAGC

GTGCAGCTCGCCGACCACTACCAGCAGAACACCCCCATCGGCGACGGCCC

CGTGCTGCTGCCCGACAACCACTACCTGAGCACCCAGTCCAAGCTGAGCA

AAGACCCCAACGAGAAGCGCGATCACATGGTCCTGCTGGAGTTCGTGACC

GCCGCCGGGATCACTCTCGGCATGGACGAGCTGTACAAGTTAATTAACGG

AAGCGGCGGGTCAGGTGGAAGTGGA;
and

GαS C-terminal α-5 peptide (can be substituted for other binding part-
ners):

(SEQ ID NO: 9)

GACACTGAGAACATCCGCCGTGTGTTCAACGACTGCCGTGACATCATTCA

GCGCATGCACCTTCGTCAGTACGAGCTGCTC.

Cell culture preparation: HEK-293T-Flp-n cells were cultured in DMEM containing 4.5 g/L D-glucose, with 10% FBS (heat inactivated) (v/v), and 1% L-glutamine, 20 mM HEPES, pH 7.5. Cells were incubated at 37° C. in a humidified atmosphere at 5% $CO_2$. Cells were allowed to grow to 95% confluency. The time to achieve confluency typically took about 24 hours when plated with $2 \times 10^6$ cells/ml in 10 ml media, and a confluent 10 cm tissue culture treated dish typically had a density of $4-6 \times 10^6$ cells/ml.

Transfection: The following reagents were combined in the listed order: 1 ml OPTI-MEM™, 20 μg DNA, 60 μg polyethylenimine (PEI). The mixture was incubated at room temperature for 15 to 30 minutes. It is noted that other transfection agents (e.g., X-TREMEGENE™, Sigma) may be used in place of PEI, but the described protocol has been optimized for PEI as a transfection agent. Cells to be transfected were washed with 10 ml PBS, and then detached from culture dishes with 1 ml 0.25% trypsin. Detached cells were resuspended in DMEM (pre-warmed to 37° C.) to a concentration of $3 \times 10^6$ cells/ml. The DNA+PEI mixture was added into 10 ml of resuspended cells and inverted gently 5 times. Transfection in suspension saved time and assured that the ratio of cells to the amount of transfection reagent remained consistent. The amount of DNA and the density of the cells was optimal for maximum cell transfection efficiency. In fact, compared to transfecting cells on a surface, transfecting cells in suspension resulted in a 51% increase in GPCR-SPASM sensor incorporation into GPVMs when using PEI. In some cases, a leucine-rich, cleavable "Lucy" tag (MRPQILLLLALLTLGLA; SEQ ID NO:10) (Chan et al. (2011) BMC Biochem 12:27; and Shepard et al. (2013) PLoS One 8:e68758, https://doi.org/10.1371/journal.pone.0068758) was added at the N-terminus of the GPCR to enhance surface GPCR expression and therefore increase GPCR expression in GPVMs.

Transfected cells were then plated onto a 15 cm tissue culture treated dish and incubated at 37° C. in a humidified atmosphere at 5% $CO_2$ for 4 hours. The 10 ml of media containing PEI was then exchanged with 20 ml of fresh DMEM (pre-warmed to 37° C. prior to exchange). The 4 hour incubation prior to media exchange was optimal for maximum transfection efficiency and minimal cell toxicity due to the PEI. In addition, the 10 ml media volume was optimal for facilitating adhesion to the surface within the 4 hour timeframe. After 24 hours of expression, fluorescence intensity and localization within the cells was assessed using a tissue culture fluorescence microscope. The fluorescence was checked every 2 hours until optimal fluorescence intensity vs. internalization was achieved.

GPMV synthesis and purification: Cells were scraped off the 15 cm tissue culture dish and transferred to a 50 ml conical tube. The standard protocol (see, Sezgin et al., 2012) synthesizes GPMVs from adherent cells, but the optimized protocol described herein synthesized GPMVs in suspension. GPMVs synthesized in suspension were purified straight from solution, thus increasing yield and eliminating the need for additional washes to release GPMVs lingering on the surface of tissue culture treated dishes when they are synthesized from adherent cells.

For 2 mM N-ethylmaleimide- (NEM-) mediated GPMV synthesis, cells were centrifuged at 300×g and resuspended in 20 ml GPMV buffer (10 mM HEPES pH 7.5, 150 mM NaCl, 2 mM CaCl$_2$), and then spun and resuspended once more. Cells were transferred to a glass Erlenmeyer flask and spiked with 2 mM NEM before being incubated in a shaking incubator at 28° C. for 2 hours. For bicine-mediated GPMV synthesis, cells were spun at 300×g and resuspended in 20 ml commercial PBS pH 7.4 (ThermoFisher Scientific). Cells were then resuspended in bicine-GPMV buffer (200 mM NaCl, 5 mM KCl, 0.5 mM MgCl$_2$, 0.75 mM CaCl$_2$, 100 mM bicine pH 8.5), transferred to a glass Erlenmeyer flask, and incubated in a shaking incubator at 28° C. for 2 hours.

For either method, the GPMV+cell solution was centrifuged at 100×g 4° C. for 10 minutes to pellet dead cells and debris, and the supernatant containing GPMVs was transferred to a 50 ml conical tube. GPMVs were maintained on ice for subsequent procedures. The GPMV solution was centrifuged at 3000×g 4° C. for 30 minutes to pellet GPMVs, which were resuspended in 10 ml HBS buffer and transferred to a 15 ml conical tube. It is noted that the standard protocol (Sezgin et al., 2012) pellets GPMVs at 20,000×g for 1 hour, whereas the present protocol has been optimized to 3000×g for 30 minutes, which is sufficient for GPMV pelleting without clumping and deformation of GPMVs. This protocol thus saves time (30 minutes vs. 1 hour) and does not require high-cost ultracentrifuge instruments. The GPMV solution was then centrifuged at 100×g 4° C. for 10 minutes to pellet any leftover dead cells and debris, since the presence of dead cells in FRET experiments can negate the change in FRET induced by ligands, due to internalized non-functional sensors within the dead cells. Thus, the protocol utilized as described herein included an additional low speed spin to exclude as many dead cells and as much debris from the solution as possible. The resulting GPMV solution was centrifuged at 3000×g 4° C. for 30 minutes to pellet GPMVs, which were resuspended in 1 ml HBS buffer or optimized buffer (20 mM HEPES pH 7.5, 25 mM KCl, 5 mM MgCl$_2$) and maintained on ice.

Experiment and data collection: mCerulean fluorescence counts (peak emission at 475 nm) of GPMVs were measured using a fluorometer (excitation 430 nm, bandpass 8 nm, emission 450-600 nm, bandpass 4 nm). GPMVs were diluted in HBS or optimized buffer to achieve 600,000 mCerulean fluorescence counts. One (1) mM ascorbic acid was added to the GPMV solution. The drug buffer was prepared by adding 1 mM ascorbic acid to 1 ml HBS or optimized buffer; the buffer was maintained on ice for subsequent procedures. GPCR ligands were diluted in the drug buffer to 10×[desired concentration]. 400 µl of GPMV solution was mixed with 44 µl of 10×ligand, and incubated at room temperature for 5 minutes. FRET spectra of GPMVs were acquired using a fluorometer (excitation 430 nm, bandpass 8 nm, emission 450-600 nm, bandpass 4 nm). The scatter background counts of the 475 nm and 525 nm emission counts were calculated by referencing the 450 nm scatter count and subtracting background emission counts from the total 475 nm and 525 nm emission counts. The FRET ratio (475 nm emission/525 nm emission) also was calculated.

Experiment and data collection in 96 well plate reader: mCerulean fluorescence counts (peak emission at 475 nm) for GPMVs in optimized buffer were acquired using a fluorometer (excitation 430 nm, bandpass 8 nm, emission 450-600 nm, bandpass 4 nm). Specifically, GPMVs were diluted in optimized buffer to achieve 2,000,000 mCerulean fluorescence counts. Ascorbic acid (1 mM) was added to the GPMV solution. Drug buffer was prepared by adding 1 mM ascorbic acid to 1 ml optimized buffer. The mixture was maintained on ice for subsequent procedures. GPCR ligands were diluted in the drug buffer to 10×[desired concentration]. In a clear-bottom 96 well plate, 10 µl of GPCR ligand or buffer was added to each well, and then 90 µl GPMVs was added to each ligand-containing well. Plates were incubated at room temperature for 5 minutes. The plates were then placed in a FLEXSTATION® 3 Multi-Mode Microplate Reader (Molecular Devices; San Jose, CA). The donor fluorophore (mCerulean, excitation 435 nm) was excited and a spectrum read was taken (bottom read, emission 500-550 nm, emission step 5 nm, cutoff 515 nm, sensitivity 40 reads per well). The acceptor fluorophore (mCitrine, excitation 485 nm) was excited and a spectrum read was taken (bottom read, emission 500-550 nm, emission step 5 nm, cutoff 515 nm, sensitivity 40 reads per well). The optical density (600 nm) was read for each well. The 525 nm emission counts from both the 435 nm and 485 nm excited spectrum were isolated. The scatter background 525 nm emission counts were calculated by referencing the optical density and subtracting background emission counts from the total 525 nm emission counts. The FRET efficiency was calculated using the following equation:

$$\left(\left(\frac{f_{A.435}}{f_{A.485}} - \frac{\varepsilon_{A.435}}{\varepsilon_{A.485}}\right) * \frac{\varepsilon_{A.485}}{\varepsilon_{D.435}}\right)$$

$F_{A.435}$=525 nm emission fluorescence counts when excited at 435 nm. $F_{A.485}$=525 nm emission fluorescence counts when excited at 485 nm. $\varepsilon_{A.435}$=molar extinction coefficient of acceptor fluorescent protein at 435 nm. $\varepsilon_{A.485}$=molar extinction coefficient of acceptor fluorescent protein at 485 nm. $\varepsilon_{D.435}$=molar extinction coefficient of donor fluorescent protein at 435 nm. $\varepsilon_{A.435}/\varepsilon_{A.485}$=0.08096. $\varepsilon_{A.485}/\varepsilon_{D.435}$=0.713.

Example 2—Purified GPMVs Incorporate SPASM GPCR Sensors

Figure 1C:
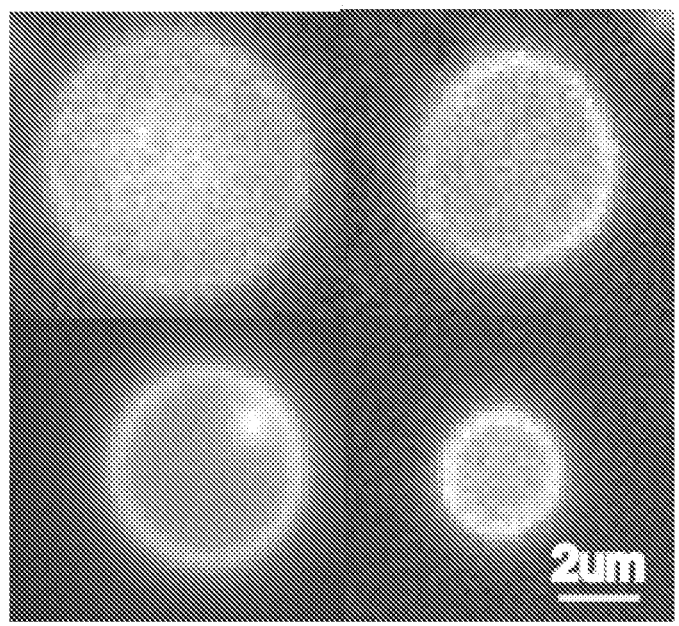
FIG. 1C is a series of fluorescence images of GPMVs incorporating a GPCR-SPASM sensor. GPMVs were synthesized from HEK293 cells expressing a beta-2 adrenergic receptor- (β2AR-) Spep sensor. Purified GPMVs were imaged with mCerulean. Scale bar=2 um.

As described elsewhere, SPASM GPCR sensors can be used to probe G protein-selective GPCR conformation in live cells (Malik et al., supra; and Semack et al., supra). GPMVs provide a convenient way of extracting a cell's plasma membrane from the cytoplasm regulation machinery, and possess the potential to incorporate GPCRs. To test the utility of GPMVs with SPASM sensors as a cell-derived agent, GPMVs were synthesized and purified from HEK293 cells expressing a β2AR-SPASM sensor (Malik et al., supra). The sensor (β2AR-Spep) contains the following from N- to C-terminus: full-length β2AR, mCitrine (FRET acceptor), a 10 nm ER/K α-helix linker, mCerulean (FRET donor), and a 27-amino acid peptide derived from the C-terminal α5 helix of the GaS subunit, all of which are separated via (Gly-Ser-Gly)$_4$ linkers (FIG. 1A). A schematic of the GPMV purification process is illustrated in FIG. 1B. Briefly, HEK293 cells expressing the β2AR-Spep sensors were washed and resuspended in GPMV buffer (10 mM HEPES pH 7.4, 150 mM NaCl, 2 mM CaCl$_2$). Cells were then incubated with 2 mM NEM for 2 hours at 30° C. Dead cells and debris were pelleted at 100×g for 10 minutes, and the supernatant containing GPMVs was extracted. GPMVs were further washed with HBS via three rounds of pelleting (3000×g for 30 minutes) and resuspension. Fluorescent imaging was then used to demonstrate that β2AR-Spep sensors were incorporated into GPMVs. The sensors were clearly visible and exhibited a nearly homogenous distribution for each GPMV (FIG. 1C). The GPMVs were spherical in shape, in agreement with the literature, and exhibited varying sizes in the range of 2-6 μm (FIG. 1C). Together, these data report the successful incorporation of SPASM GPCR sensors into GPMVs.

Example 3—GPMV-Incorporated Membrane Proteins are Functional

Figure 2A:
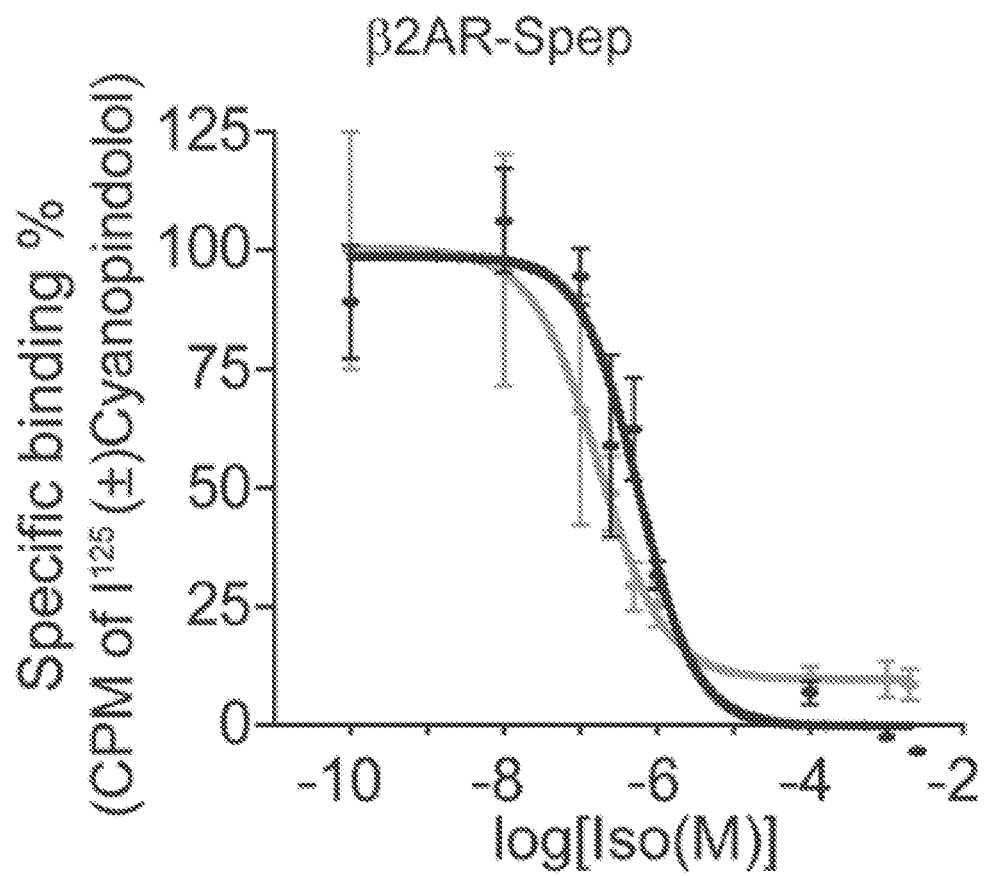
FIG. 2A is a graph plotting competition of radioligand binding to GPMV-β2AR-Spep sensors via isoproterenol. GPMVs incorporating 20 fmol of indicated β2AR-Spep sensors were stimulated with increasing concentrations of isoproterenol, in the presence of $I^{125}$-(±)-Cyanopindolol (500 nM).
Figure 2B:
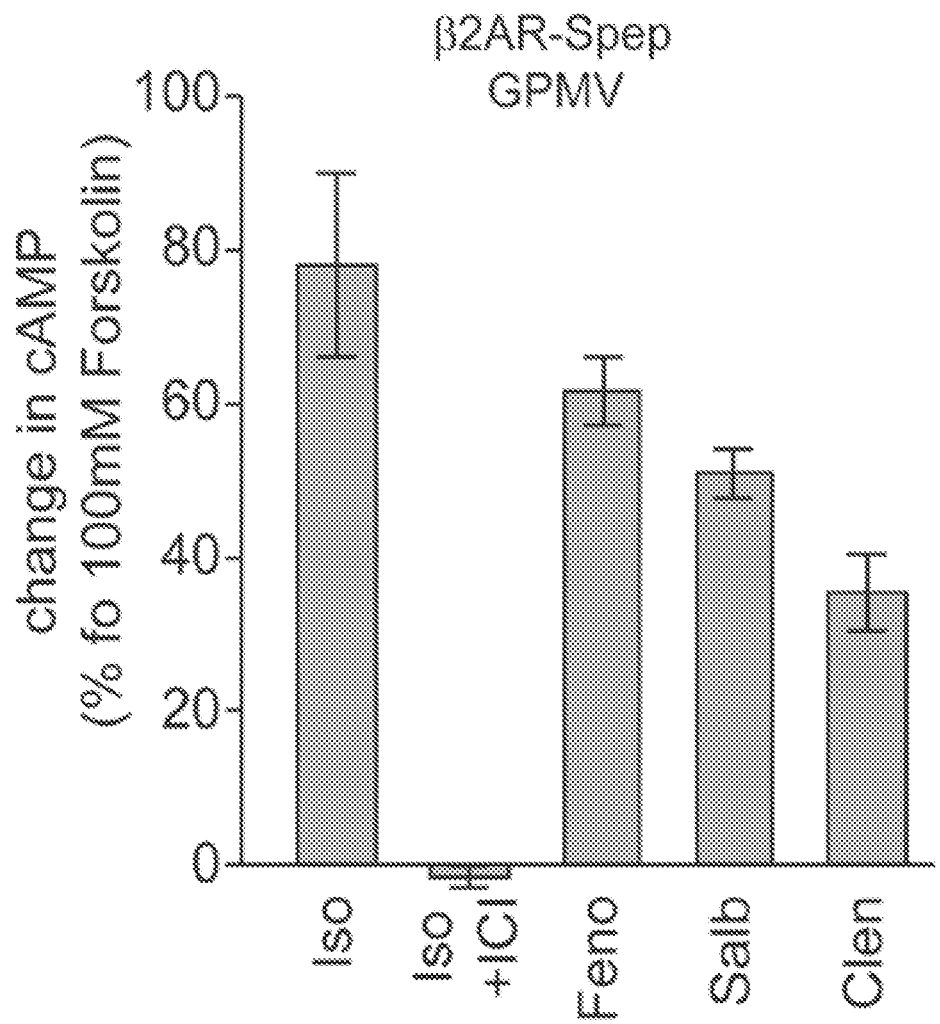
FIG. 2B is a graph plotting cAMP accumulation in GPMV-β2AR-Spep sensors stimulated with saturating concentrations of isoproterenol (Iso; 10 μM), fenoterol (Feno; 10 μM), salbutamol (Salb; 10 μM), clenbuterol (Clen; 10 μM), and isoproterenol with ICI 118,551 (Iso+ICI; 10 μM and 1 μM, respectively). The increase in cAMP is expressed as a percentage of the forskolin-stimulated cAMP response (Fsk).

The functionality of the β2AR-Spep sensors in GPMVs was then investigated. In particular, the function of the β2AR-Spep sensor was tested by a combination of radioligand binding and concentration-response analyses (FIG. 2A). β2AR-Spep sensors incorporated in GPMVs (GPMV-β2AR-Spep) bound robustly to both the orthosteric antagonist [$^{125}$I]cyanopindolol and the agonist isoproterenol. The affinities (pKd and pKi) for [$^{125}$I]cyanopindolol and isoproterenol were 6.59 and 8.59, respectively. Notably, under the same concentration of β2AR-Spep sensors (monitored via mCerulean fluorescence counts), GPMVs had a twenty-fold higher ligand binding capacity than purified membrane preparations (Gupte et al. (2017) Proc. Natl. Acad. Sci. USA 114, 3756-3761), suggesting significantly higher levels of functional GPCR. This may stem from the fact that the GPMVs originated exclusively from the plasma membrane, whereas purified membrane extracts also contain intracellular membrane components such as the ER and/or golgi. β2AR-Spep sensors in the ER or golgi would be non-functional and unable to bind to GPCR ligands. Thus, a portion of the β2AR-Spep sensors included in the membrane extracts could be non-mature and non-functional, while most of the GPCRs incorporated into the GPMVs are mature/functional receptors that have been localized to the plasma membrane. Hence, the data provided herein demonstrate that the fraction of functional β2AR-Spep sensors is significantly higher in GPMVs than in membrane extracts. Additionally, stimulating GPMV-β2AR-Spep sensors with isoproterenol induced cAMP synthesis, indicating that both the endogenous Gα subunits and the endogenous adenylate cyclase present in the GPMVs were functional (FIG. 2B). Together, these data show that the membrane proteins incorporated in GPMVs, including SPASM GPCR sensors, retain their function.

Example 4—Characterization of the FRET Response in Purified GPMV-β2AR-Spep

Figure 3B:
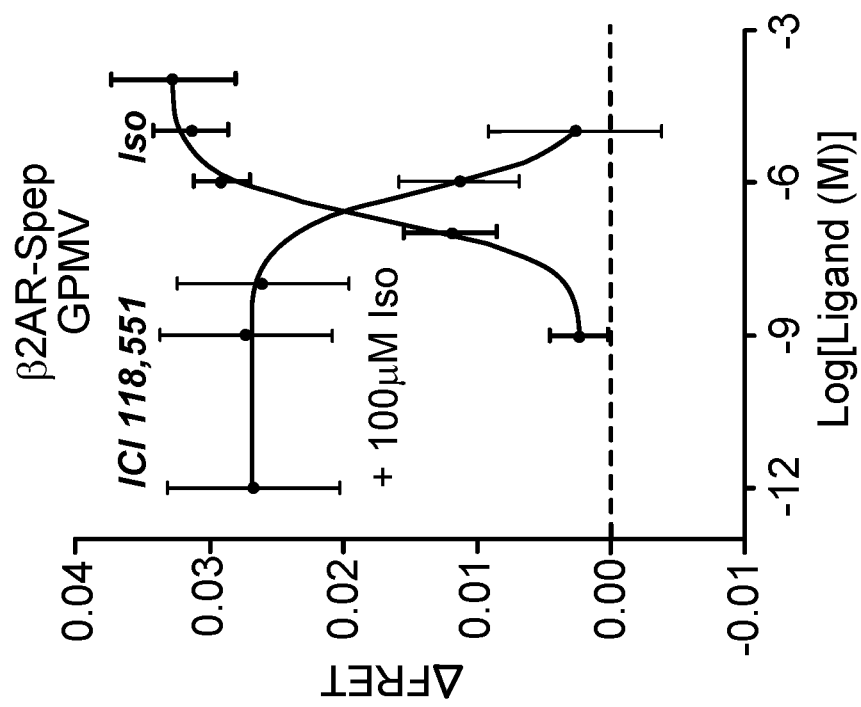
FIG. 3B is a graph plotting dose-dependent changes in GPMV-β2AR-Spep FRET measurements. GPMV-β2AR-Spep sensors were stimulated with increasing concentrations of isoproterenol (black) or increasing concentrations of ICI 118,551 (gray). GPMV-β2AR-Spep sensors were stimulated with a saturating concentration of isoproterenol (100 μM)
Figure 3A:
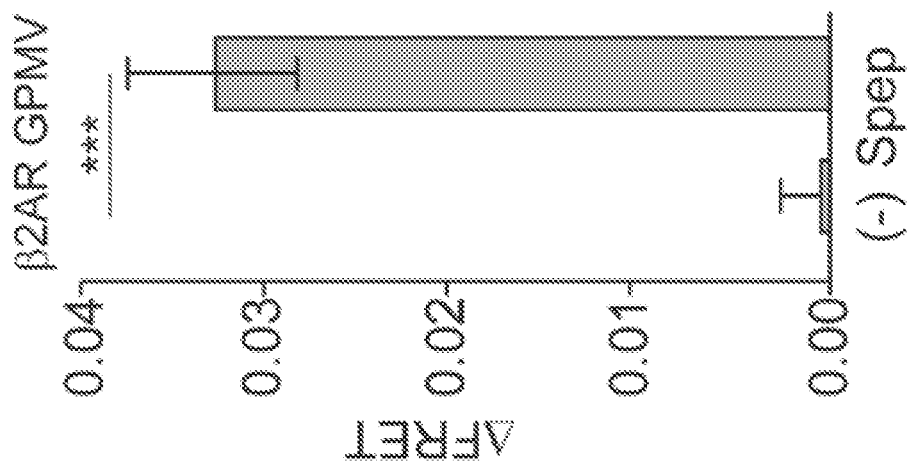
FIG. 3A is a graph plotting the change in FRET ratio following isoproterenol stimulation. FRET measurements were taken with GPMV-β2AR-SPASM sensors tethered to the C terminal α5 helix of the GαS subunit (Spep) or a no-peptide control (–). The S-pep sensors exhibited a gain in FRET following isoproterenol (100 μM) stimulation, whereas the No-pep sensors did not show an increase.

Studies were then undertaken to assess the utility of GPMVs incorporating SPASM GPCR sensors (GPMV sensors) as a cell free FRET-based assay for monitoring GPCR-α5 helix interaction. Toward this goal, the FRET measurements of SPASM GPCR sensors in GPMVs were characterized. SPASM GPCR sensors report the interaction between GPCRs and the C terminal α5 helix through FRET measurements (Malik et al., supra; and Semack et al., supra). As described elsewhere, β2AR-Spep sensors exhibit an agonist-dependent gain in FRET in live cells (Semack et al. (2016) J. Vis. Exp. 11554696, 1-11). The studies described herein showed that similarly, purified GPMV-β2AR-Spep sensors display a gain in FRET when stimulated with isoproterenol, comparable to the gain described for live cells (FIG. 3A). The observed gain in FRET was specific for the C terminal α5 helix of the GαS subunit, demonstrating that the sensor probes G protein-selective GPCR conformations. Specificity of the gain in FRET was further demonstrated by the concentration dependence of the isoproterenol response (FIG. 3B). Additionally, the orthosteric antagonist ICI 118, 551 competitively suppressed the gain in FRET observed at saturating isoproterenol concentrations (100 μM). These observations exemplify that the FRET measurements observed with GPMV-β2AR-Spep sensors can probe the interaction between PAR and the C terminal α5 of the GαS subunit. Together, these data demonstrate the utility of GPMV sensors as a cell free FRET-based assay for monitoring GPCR-α5 helix interaction and G protein-selective GPCR conformations.

Example 5—Advantages of GPMV Over Live Cell Experiments

Figure 4A:
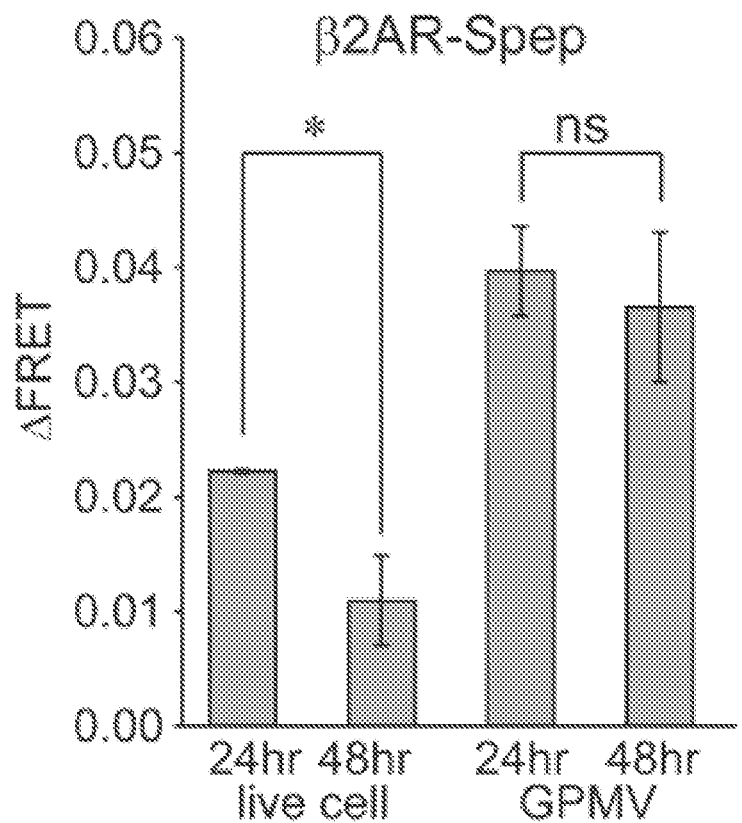
FIG. 4A is a graph plotting GPMV sensitivity to GPCR-SPASM sensor expression. GPMVs were synthesized from HEK293 cells expressing (24 hour expression time) or extensively overexpressing (48 hour expression time) β2AR-Spep sensors, and stimulated with isoproterenol. Extensively overexpressing β2AR-Spep sensors drastically decreased the level of ΔFRET in live cells. GPMV-β2AR-Spep sensors synthesized from extensively overexpressing HEK293 cells did not exhibit a significant decrease in ΔFRET levels. GPMV FRET measurements were not sensitive to duration of either sensor expression in cells or ligand stimulation.
Figure 4B:
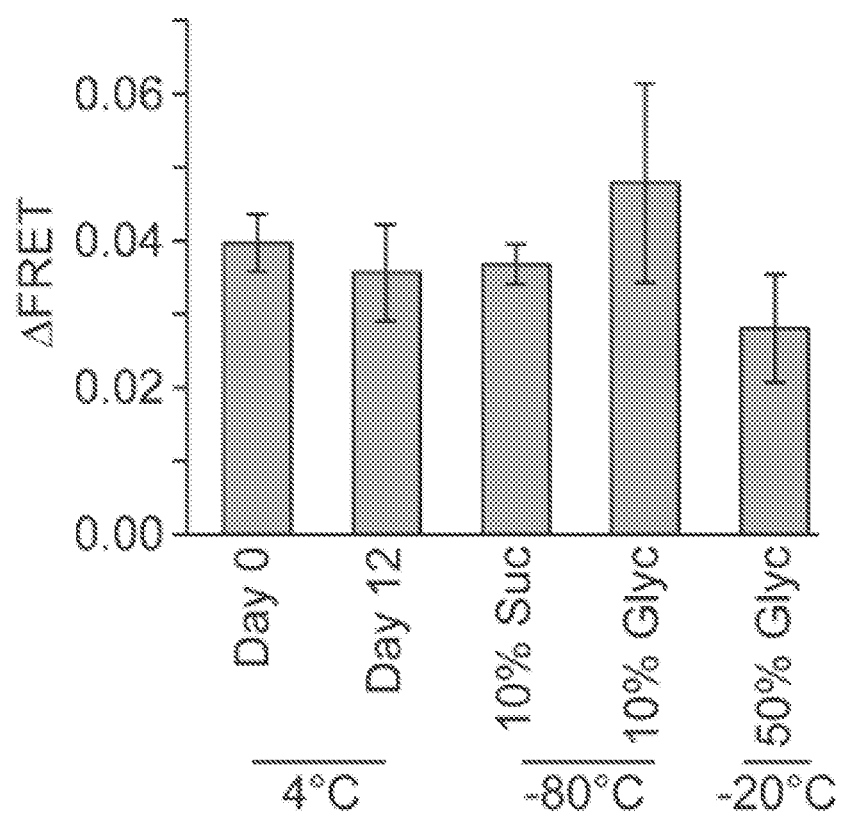
FIG. 4B is a graph plotting FRET measurements for GPMV-β2AR-Spep sensors that were maintained on ice or stored frozen with 10% sucrose, 10% glycerol, or 50% glycerol for twelve days. Stored GPMV-β2AR-Spep sensors were thawed and stimulated with isoproterenol (100 uM). ΔFRET levels of GPMV-β2AR-Spep sensors in all storage conditions were comparable with that of a fresh batch. Thus, the GPMVs were stable over a long period of time and post freeze-thaw.

Due to the dynamic nature of the cell regulation machinery, SPASM-FRET measurements in live cells are sensitive to time-dependent factors such as expression levels and stimulation length. In contrast, GPMV-β2AR-Spep sensors showed robust response regardless of these elements. In live cells, the expression level of β2AR-Spep influenced FRET measurements, where excessive overexpression tended to saturate the system and decrease the dynamic range of ΔFRET (FIG. 4A). Conversely, GPMVs synthesized from HEK293 cells excessively overexpressing (48 hour expression) β2AR-Spep exhibited the same level of ΔFRET as GPMVs synthesized from much lower expressing (24 hour expression) cells. Thus, the minimal sensitivity of GPMV sensors to time-dependent factors provides a higher level of consistency in FRET measurements than live cells. Further, purified GPMV-β2AR-Spep sensors sustained a constant level of agonist-specific ΔFRET for 12 days when preserved on ice, representing a high level of stability. Additionally, these sensors could be frozen under various conditions and did not exhibit any significant loss in function post-thawing (FIG. 4B). The ability to stably freeze-thaw GPMV-β2AR-Spep allows for large-scale production and storage of the reagent, providing multiple experiments from a common batch. Collectively, these observations exemplified the consistency, stability, and scalability of GPMV sensors. In addition, the use of a modified low salt buffer (20 mM HEPES pH 7.4, 25 mM KCl, 5 mM $MgCl_2$) provides a higher ΔFRET (~0.07), thereby substantially increasing the dynamic range of the GPMV-based assay. GPMVs can also be permeabilized with detergents (e.g., saponin) to modulate the intra-GPMV environment. For example, permeabilization can be used to study the influence of soluble biologics and small-molecules, such as nucleotides, on GPCR signaling in a native environment.

Example 6—Measurement of Intrinsic Efficacy Utilizing SPASM GPCR Sensors Integrated into GPMVs A ligand's ability to elicit a specific downstream response is termed "ligand efficacy," and is dictated by the cellular context and the ligand's "intrinsic efficacy" (Kenakin (2014) A Pharmacology Primer: Techniques for More Effective and Strategic Drug Discovery: Fourth Edition, Elsevier, Inc.). The "intrinsic efficacy" is a ligand-specific term defining the level of stimulus that a bound ligand exerts on a single receptor (Kenakin, supra). However, measurement of intrinsic efficacy has eluded researchers due to the multitude of factors that regulate GPCR signaling (Salazar et al. (2007)

Figure 5A:
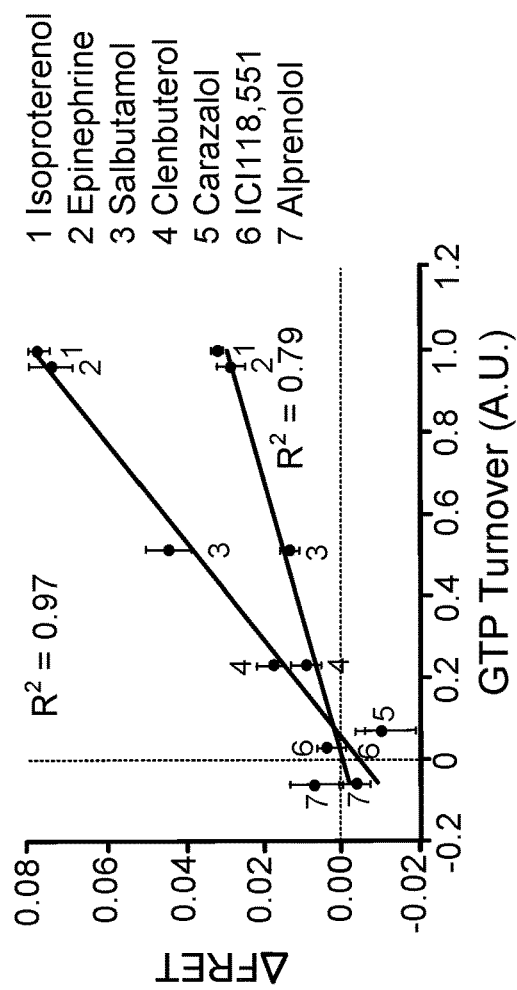
FIGS. 5A and 5B are graphs showing that GPMV-β2AR-Spep ΔFRET correlates linearly with molecular efficacy. GPMV-β2AR-Spep sensors were stimulated with various ligands, and the ΔFRET values were plotted against previously documented measurements of ligand intrinsic efficacies (Gregorio et al., supra). Ligand induced ΔFRET correlated strongly with both the molecular efficacy (FIG. 5A, $R^2=0.96$~0.99) and the ligands' ability to induce GTP turnover via purified β2AR-GaS protein complex in vitro (FIG. 5B, $R^2=0.79$~0.97). Upper lines (black): optimized buffer (20 mM HEPES pH 7.4, 25 mM KCl, 5 mM $MgCl_2$). Lower lines (gray): HBS buffer (20 mM HEPES pH 7.4, 5 mM KCl, 145 mM NaCl, 2 mM $CaCl_2$, 1 mM $MgCl_2$). Error bars denote s.e.m. Data are derived from at least three independent experiments, with at least three replicates per condition.
Figure 5B:
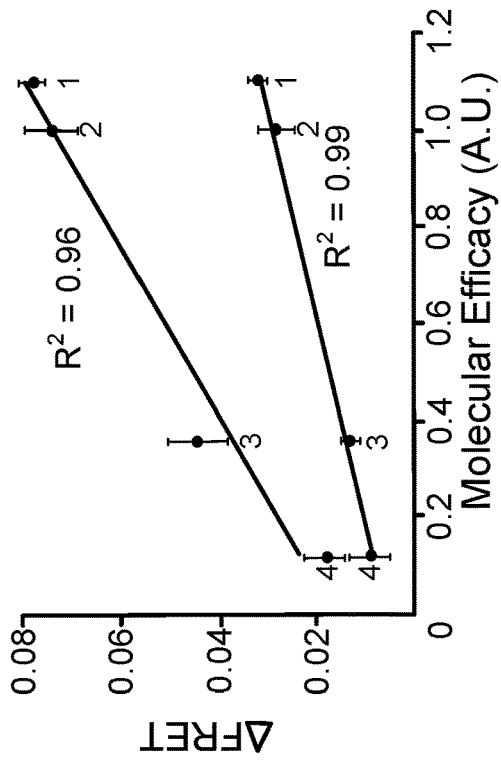

*Biochim. Biophys. Acta—Biomembr.* 1768, 1006-1018). The closest generalizable method of measuring intrinsic efficacy to date is monitoring G protein activation (Harrison and Traynor, supra; Denis et al., supra; and Gregorio et al., supra). GPCR-mediated activation of G proteins is measured utilizing live cells, crude membrane extracts, or purified receptors and G proteins. Both systems present technical limitations that restrict their use as reliable and scalable high-throughput assays. Purifying GPCRs and G proteins is a multiple-step process, which requires laborious optimizations for each procedure. Further, the inherent heterogeneity of live cells and crude membrane extracts introduces inconsistency between observations. As such, current methods of measuring intrinsic efficacy either requires high cost or suffers low reliability. Here The utility of the GPMV sensors described herein for measuring intrinsic efficacy was therefore assessed. Toward that end, FRET measurements in GPMV-β2AR-Spep sensors were monitored following stimulation via ligands with efficacy profiles ranging from inverse agonists to full agonists (FIGS. 5A and 5B). FRET measurements in agonist-stimulated GPMV-β2AR-Spep sensors correlated strongly ($R^2=0.99$) with intrinsic efficacies and G protein activation documented elsewhere (Gregorio et al., supra). These data demonstrated the utility of GPMV sensors as a modular assay that reports the efficacies of GPCR ligands through FRET measurements. The scalable production of GPMV sensors, alongside the high level of consistency and stability in FRET measurements, provides a novel and facile cell-derived assay for measuring the intrinsic efficacies of GPCR ligands.

Example 7—Buffer Optimization

Salts such as sodium and magnesium can affect the function of GPCR by acting as allosteric modulators (see, e.g., Ye et al. (2018) *Nat Commun* 9:1372; |DOI: 10.1038/s41467-018-03314-9). The possibility of increasing the dynamic range of the GPMV-GPCR-FRET sensors by altering the experimental salt concentrations was therefore assessed. Substituting HEPES buffered saline (20 mM HEPES pH 7.4, 5 mM KCl, 145 mM NaCl, 2 mM $CaCl_2$, 1 mM $MgCl_2$) with an optimized buffer (20 mM HEPES pH 7.4, 25 mM KCl, 5 mM $MgCl_2$) significantly increased the dynamic range of the FRET measurements. It is noted that the optimized buffer excluded sodium, a known negative allosteric modulator (Ye et al., supra). FRET experiments with multiple ligands were carried out in low and high salt conditions, and the results were compared with previously documented measurements of ligand intrinsic efficacies (Gregorio et al., supra). Though FRET measurement for a common ligand differed drastically between low and high salt concentrations, FRET measurements for all ligands in both low and high salt conditions correlated strongly with both the ligands' ability to induce molecular efficacy (FIG. 5A, $R^2=0.96$~$0.99$) and GTP turnover via purified β2AR-GaS protein complex in vitro (FIG. 5B, $R^2=0.79$~$0.97$). These results indicated that salt concentration can significantly influence the intrinsic efficacy maxima of GPCR ligands, but do not alter the relative intrinsic efficacies between GPCR ligands.

Example 8—Comparison with Parameter that Dictate Classical Efficacy

Figure 6:
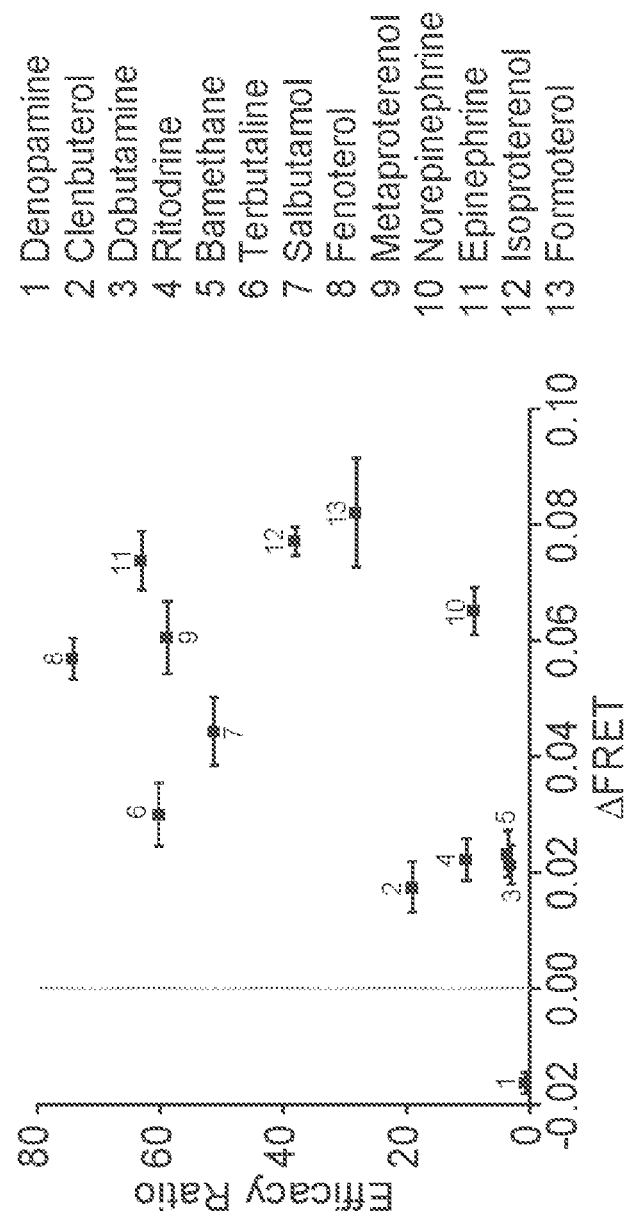
FIG. 6 is a graph demonstrating that GPMV-β2AR-Spep ΔFRET does not correlate with classical efficacy measurements. GPMV-β2AR-Spep sensors were stimulated with various ligands, and the ΔFRET were plotted against previously documented ligand efficacy ratios (Baker (2010) Br. J. Pharmacol. 160(5):1048-61). Error bars denote s.e.m. Data are derived from at least three independent experiments, with at least three replicates per condition. $R^2=0.29$ for efficacy ratio vs ΔFRET.

FRET measurements also were compared with results of a study that measured the efficacies of various ligands using classic pharmacological methods (Baker, supra). The study utilized cell-based assays generally utilized in classical pharmacology to derive the parameter "efficacy ratio." Though the experimental measurements and parameters described in the study are generally used in classical pharmacology as a measurement of ligand efficacy, the readout of these cell-based assays are several levels removed from the actual receptor-G protein interaction. Thus, it was observed that the FRET measurements, which represent ligand intrinsic efficacies as established above (FIGS. 5A and 5B), did not correlate with the documented efficacy ratios (FIG. 6) or with experimental measurements dictating the efficacy ratios (FIGS. 7A-7C). These observations present an example of the importance of utilizing tools that investigate phenomena occurring at the level of the receptor-G protein complex when studying ligand intrinsic efficacy, advocating for the utility of the GPMV-GPCR-FRET sensors described herein, as the readout of these sensors is dictated directly by the ligand's effect on the function of the receptor.

Example 9—GPMV-GPCR Sensors can be Utilized in a High-Throughput Manner

Figure 8:
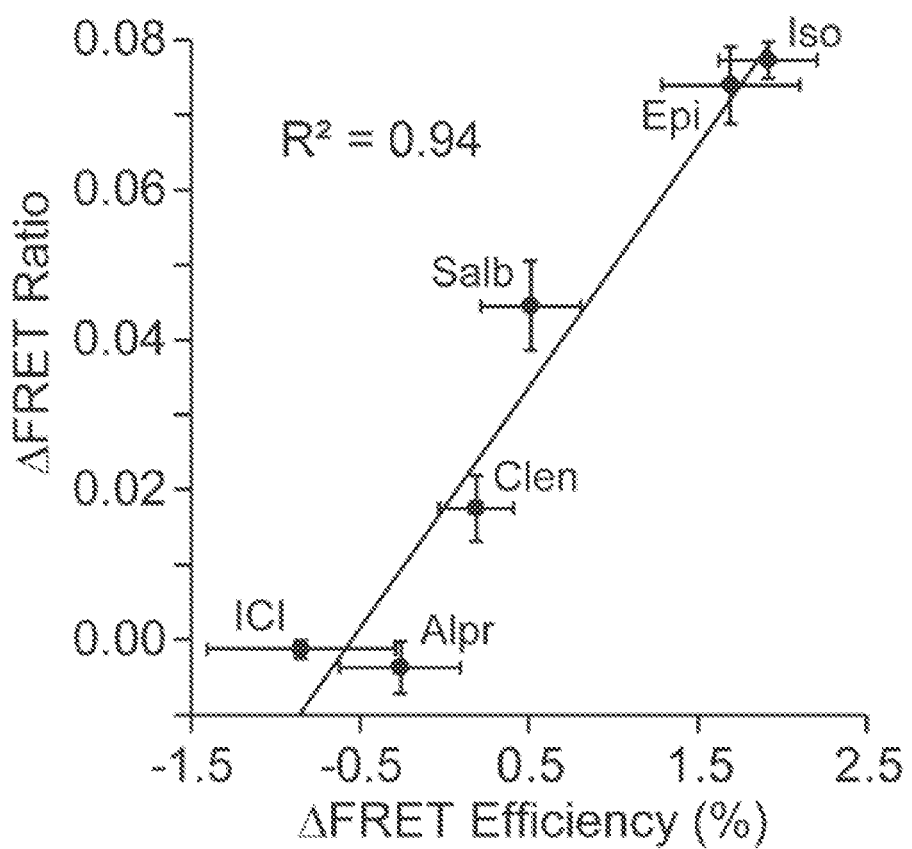
FIG. 8 is a graph showing that GPMV-GPCR sensors can be utilized in a high-throughput manner. Fluorescence measurements of ligand-treated GPMV-β2AR-Spep sensors were obtained using a high-throughput 96-well plate reader. ΔFRET efficiencies as described elsewhere (Toropova et al. (2014) Elife 3:e03372 DOI:10.7554/eLife.03372) were calculated and plotted against the ΔFRET ratios shown in FIGS. 5A and 5B. Calculated ΔFRET efficacies correlates linearly with ΔFRET ratios ($R^2=0.94$).

GPMV-β2AR-Spep sensors were stimulated with various ligands, and fluorescence measurements were taken utilizing a high-throughput 96-well plate reader. Measurements taken via the plate reader were used to calculate the ΔFRET efficiencies as described in elsewhere (Toropova et al., supra), and plotted against the ΔFRET ratios shown in FIGS. 5A and 5B. Calculated ΔFRET ratios correlated linearly ($R^2=0.97$) with ΔFRET efficiencies (FIG. 8), demonstrating that GPMV-GPCR sensors can be utilized in a high-throughput manner.

Example 10—GPMV Synthesis Utilizing Bicine

Figure 9:
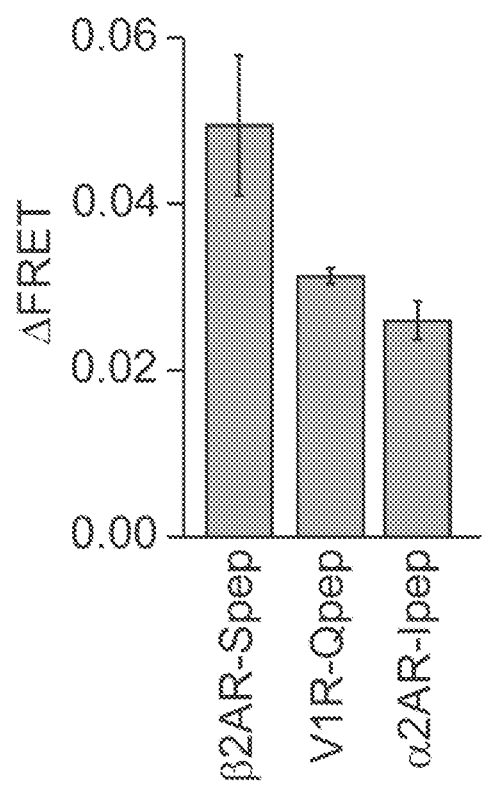
FIG. 9 is a graph demonstrating that GPMV-GPCR sensors are generally applicable to a variety of GPCR and G proteins. GPMVs, incorporating the β2AR-Spep, vasopressin) receptor- (V1R-) Qpep, and alpha-1A adrenergic receptor- (α1AR-) Ipep sensors, were synthesized by the bicine-mediated method. The sensors were treated with their respective full agonists (100 μM isoproterenol, 100 nM AVP, and 100 μM epinephrine, respectively), and changes in FRET were measured.

An alternative method of synthesizing GPMVs utilizes a buffer containing of various salts and the organic compound, bicine, as a buffering agent (see, Del Piccolo et al. (2012) *Anal Chem* 84(20):8650-8655). An advantage of this method is that it does not use any chemical agents that might cross-link to free cysteines. Utilizing the bicine-mediated GPMV synthesis method, GPMVs were synthesized to incorporate various GPMV-GPCR sensors. ΔFRET measurements (FIG. 9) were comparable to those observed for GPMVs synthesized with the NEM-mediated method.

Example 11—GPMV-GPCR Sensors are Generally Applicable to a Variety of GPCRs and G Proteins GPMVs incorporating various GPCR sensors (β2AR, V1R, and α1AR) were synthesized using the bicine-mediated method. Each sensor was tethered to the C-terminal α5-helix peptide from its cognate G-protein (Gs, Gq, and Gi, respectively). The GPMV-GPCR sensors were then treated with their respective full agonists (100 μM isoproterenol, 100 nM [Arg[8]]vasopressin (AVP), and 100 μM epinephrine, respectively), and changes in FRET was measured. The GPMV-GPCR sensors exhibited ΔFRET levels (FIG. 9) comparable to those obtained in the other experiments described herein, indicating that GPMV-GPCR sensors are generally applicable to a variety of GPCR, regardless of the type of cognate G protein.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A giant plasma membrane vesicle (GPMV) comprising a membrane-associated polypeptide, wherein the membrane-associated polypeptide comprises a target G protein-coupled receptor (GPCR), a linker comprising an amino acid sequence flanked by a FRET donor and a FRET acceptor, and a ligand for the target GPCR, wherein the linker separates the target GPCR from the ligand.

2. The GPMV of claim 1, wherein the linker is about 10 nm to about 30 nm in length.

3. The GPMV of claim 1, wherein the linker comprises an ER/K sequence comprising a substantially repeating sequence of glutamic acid, arginine, and lysine residues, and is about 50 to about 250 amino acids in length.

4. The GPMV of claim 3, wherein the linker comprises the amino acid sequence set forth in SEQ ID NO:2, or comprises a sequence that is at least 95% identical to the sequence set forth in SEQ ID NO:2.

5. The GPMV of claim 1, wherein the ligand is a peptide, polypeptide, protein, or protein domain.

6. The GPMV of claim 1, wherein the membrane-associated polypeptide further comprises a (Gly-Ser-Gly)$_{2-4}$ amino acid sequence on either side of the FRET donor and the FRET acceptor.

7. The GPMV of claim 1, wherein the membrane-associated polypeptide comprises, in order from amino terminus to carboxy terminus:
   the target GPCR;
   a first (Gly-Ser-Gly)$_{2-4}$ amino acid sequence;
   a FRET donor or acceptor;
   a second (Gly-Ser-Gly)$_{2-4}$ amino acid sequence;
   the linker;
   a third (Gly-Ser-Gly)$_{2-4}$ amino acid sequence;
   a partner for the FRET donor or acceptor;
   a fourth (Gly-Ser-Gly)$_{2-4}$ amino acid sequence; and
   the ligand for the target GPCR.

8. A method for quantifying the intrinsic efficacy of a compound for a target GPCR, the method comprising:
   (a) providing a GPMV sensor, the sensor comprising a GPMV comprising a membrane-associated polypeptide, wherein the membrane-associated polypeptide comprises a target GPCR, a linker comprising an amino acid sequence flanked by a FRET donor and a FRET acceptor, and a ligand for the target GPCR, wherein the linker separates the target GPCR from the ligand;
   (b) measuring an initial FRET ratio for the sensor;
   (c) contacting the sensor with a compound that interacts with the target GPCR;
   (d) measuring a test FRET ratio for the sensor; and
   (e) calculating the intrinsic efficacy of the compound for the target GPCR based on the difference between the test FRET ratio and the initial FRET ratio.

9. The method of claim 8, wherein the linker comprises an ER/K sequence comprising a substantially repeating sequence of glutamic acid, arginine, and lysine residues, and is about 50 to about 250 amino acids in length.

10. The method of claim 9, wherein the linker comprises the amino acid sequence set forth in SEQ ID NO:2, or comprises a sequence that is at least 95% identical to the sequence set forth in SEQ ID NO:2.

11. The method of claim 8, wherein the ligand is a peptide, polypeptide, protein, or protein domain.

12. The method of claim 8, wherein the membrane-associated polypeptide further comprises a (Gly-Ser-Gly)$_{2-4}$ amino acid sequence on either side of the FRET donor and the FRET acceptor.

13. The method of claim 8, wherein the membrane-associated polypeptide comprises, in order from amino terminus to carboxy terminus:
the target GPCR;
a first (Gly-Ser-Gly)$_{2-4}$ amino acid sequence;
a FRET donor or acceptor;
a second (Gly-Ser-Gly)$_{2-4}$ amino acid sequence;
the linker;
a third (Gly-Ser-Gly)$_{2-4}$ amino acid sequence;
a partner for the FRET donor or acceptor;
a fourth (Gly-Ser-Gly)$_{2-4}$ amino acid sequence; and
the receptor partner ligand for the target GPCR.

14. A method for identifying a compound that interacts with a target GPCR, the method comprising:
(a) providing a GPMV sensor, the sensor comprising a GPMV comprising a membrane-associated polypeptide, wherein the membrane-associated polypeptide comprises a target GPCR, a linker comprising an amino acid sequence flanked by a FRET donor and a FRET acceptor, and a ligand for the target GPCR, wherein the linker separates the target GPCR from the ligand;
(b) measuring an initial FRET ratio for the sensor;
(c) contacting the sensor with a candidate compound;
(d) measuring a test FRET ratio for the sensor; and
(e) identifying the candidate compound as interacting with the target GPCR when the test FRET ratio is altered by at least 0.5% as compared to the initial FRET ratio.

15. The method of claim 14, wherein the linker comprises an ER/K sequence comprising a substantially repeating sequence of glutamic acid, arginine, and lysine residues, and is about 50 to about 250 amino acids in length.

16. The method of claim 15, wherein the linker comprises the amino acid sequence set forth in SEQ ID NO:2, or comprises a sequence that is at least 95% identical to the sequence set forth in SEQ ID NO:2.

17. The method of claim 14, wherein the ligand is a peptide, polypeptide, protein, or protein domain.

18. The method of claim 14, wherein the membrane-associated polypeptide further comprises a (Gly-Ser-Gly)$_{2-4}$ amino acid sequence on either side of the FRET donor and the FRET acceptor.

19. The method of claim 14, wherein the membrane-associated polypeptide comprises, in order from amino terminus to carboxy terminus:
the target GPCR;
a first (Gly-Ser-Gly)$_{2-4}$ amino acid sequence;
a FRET donor or acceptor;
a second (Gly-Ser-Gly)$_{2-4}$ amino acid sequence;
the linker;
a third (Gly-Ser-Gly)$_{2-4}$ amino acid sequence;
a partner for the FRET donor or acceptor;
a fourth (Gly-Ser-Gly)$_{2-4}$ amino acid sequence; and
the ligand for the target GPCR.

20. The method of claim 14, further comprising providing two or more GPMV sensors, each comprising a different target GPCR, measuring initial and test FRET ratios for each GPMV sensor, and identifying the candidate compound as a GPCR-specific ligand when at least some of the test FRET ratios are not altered by at least 0.5% as compared to the initial FRET ratios.

* * * * *

UNITED STATES PATENT AND TRADEMARK OFFICE
CERTIFICATE OF CORRECTION

| | | |
|---|---|---|
| PATENT NO. | : 12,098,184 B2 | |
| APPLICATION NO. | : 16/769852 | |
| DATED | : September 24, 2024 | |
| INVENTOR(S) | : Sivaraj Sivaramakrishnan and Keehun Kim | |

It is certified that error appears in the above-identified patent and that said Letters Patent is hereby corrected as shown below:

On the Title Page

Item (56), References Cited, Other Publications, Line 17, delete "B:" and insert therefor -- B. --;

Item (56), References Cited, Other Publications, Line 25, delete "Biol," and insert therefor -- Biol. --;

In the Claims

Column 33, Line 12, Claim 13, delete "receptor partner".

Signed and Sealed this
Twelfth Day of November, 2024

*Katherine Kelly Vidal*

Katherine Kelly Vidal
*Director of the United States Patent and Trademark Office*